(12) United States Patent
Elzik et al.

(10) Patent No.: US 11,464,666 B2
(45) Date of Patent: Oct. 11, 2022

(54) HAND ELEVATION DEVICE AND METHODS OF USE

(71) Applicants: St. Joseph Health System, Irvine, CA (US); Innovation Lab, LLC, Newport Beach, CA (US)

(72) Inventors: Mark E. Elzik, Irvine, CA (US); Thomas J. Graham, Cleveland, OH (US); Marc Tewfik Habib, Redondo Beach, CA (US); Nicole Marie Weikert, Huntington Beach, CA (US); David G. Matsuura, Del Mar, CA (US); Myk Wayne Lum, Irvine, CA (US); Aung Khin Soe Win, Alahambra, CA (US)

(73) Assignees: Innovation Lab, LLC, La Palma, CA (US); St. Joseph Health System, Irvine, CA (US)

( * ) Notice: Subject to any disclaimer, the term of this patent is extended or adjusted under 35 U.S.C. 154(b) by 427 days.

(21) Appl. No.: 15/751,670

(22) PCT Filed: Aug. 11, 2016

(86) PCT No.: PCT/US2016/046617
§ 371 (c)(1),
(2) Date: Feb. 9, 2018

(87) PCT Pub. No.: WO2017/027737
PCT Pub. Date: Feb. 16, 2017

(65) Prior Publication Data
US 2018/0228637 A1  Aug. 16, 2018

Related U.S. Application Data

(60) Provisional application No. 62/203,763, filed on Aug. 11, 2015.

(51) Int. Cl.
*A61F 5/37* (2006.01)

(52) U.S. Cl.
CPC ................................. *A61F 5/3738* (2013.01)

(58) Field of Classification Search
CPC ...... A61F 5/3738; A61F 5/37; A61F 5/05858; A61F 5/058; A61F 5/05866;
(Continued)

(56) References Cited

U.S. PATENT DOCUMENTS 2,875,754 A * 3/1959 Messer ................. A61F 5/3738
602/21
3,554,194 A * 1/1971 Johnson ............... A61F 5/3738
602/4
(Continued)

*Primary Examiner* — Erin Deery
*Assistant Examiner* — Robin Han
(74) *Attorney, Agent, or Firm* — Mintz Levin Cohn Ferris Glovsky and Popeo, P.C.

(57) ABSTRACT

A hand elevation device is described that can position and secure a recovering hand and/or wrist for improved recovery. For example, the hand elevation device can secure a hand and/or wrist that has been operated on or injured in a therapeutic position. The therapeutic position can include the hand being positioned above an elevation line. The elevation line can include a horizontal line that intersects the heart of the user wearing the hand elevation device.

16 Claims, 16 Drawing Sheets

(58) Field of Classification Search
CPC ...... A61F 2007/0029; A61F 2007/0034; A61F 7/00; A61F 5/373; A61F 5/3723; A61F 5/3753
USPC .................... 602/4, 5, 20, 21; 128/878; 2/16
See application file for complete search history.

(56) References Cited

U.S. PATENT DOCUMENTS

| | | | |
|---|---|---|---|
| 4,285,337 A | 8/1981 | Cosentino | |
| 4,598,702 A * | 7/1986 | Lilla | A61F 5/3738 602/4 |
| 5,413,552 A | 5/1995 | Iwuala | |
| 5,464,383 A * | 11/1995 | Padden | A61F 5/3753 128/878 |
| 5,569,172 A * | 10/1996 | Padden | A61F 5/3753 128/878 |
| 6,099,489 A * | 8/2000 | Herzberg | A61F 13/10 2/45 |
| 7,052,478 B1 * | 5/2006 | Bodenschatz | A61F 5/3738 602/5 |
| 7,789,842 B2 | 9/2010 | Bittar | |
| 8,196,588 B1 | 6/2012 | Krenzel | |
| 2003/0135141 A1 * | 7/2003 | Berhorst | A61F 5/3723 602/20 |
| 2004/0186539 A1 | 9/2004 | Nozik et al. | |
| 2006/0013976 A1 * | 1/2006 | Leiss | A61F 13/128 428/36.1 |
| 2007/0043313 A1 | 2/2007 | Avon | |
| 2008/0015479 A1 * | 1/2008 | Soscia | A61F 5/3738 602/4 |
| 2009/0088673 A1 | 4/2009 | Bittar | |
| 2010/0121237 A1 | 5/2010 | Ylisela et al. | |
| 2012/0022417 A1 * | 1/2012 | Thompson | A61F 5/05808 602/4 |
| 2014/0259334 A1 * | 9/2014 | Mitchell | A41D 23/00 2/461 |

* cited by examiner

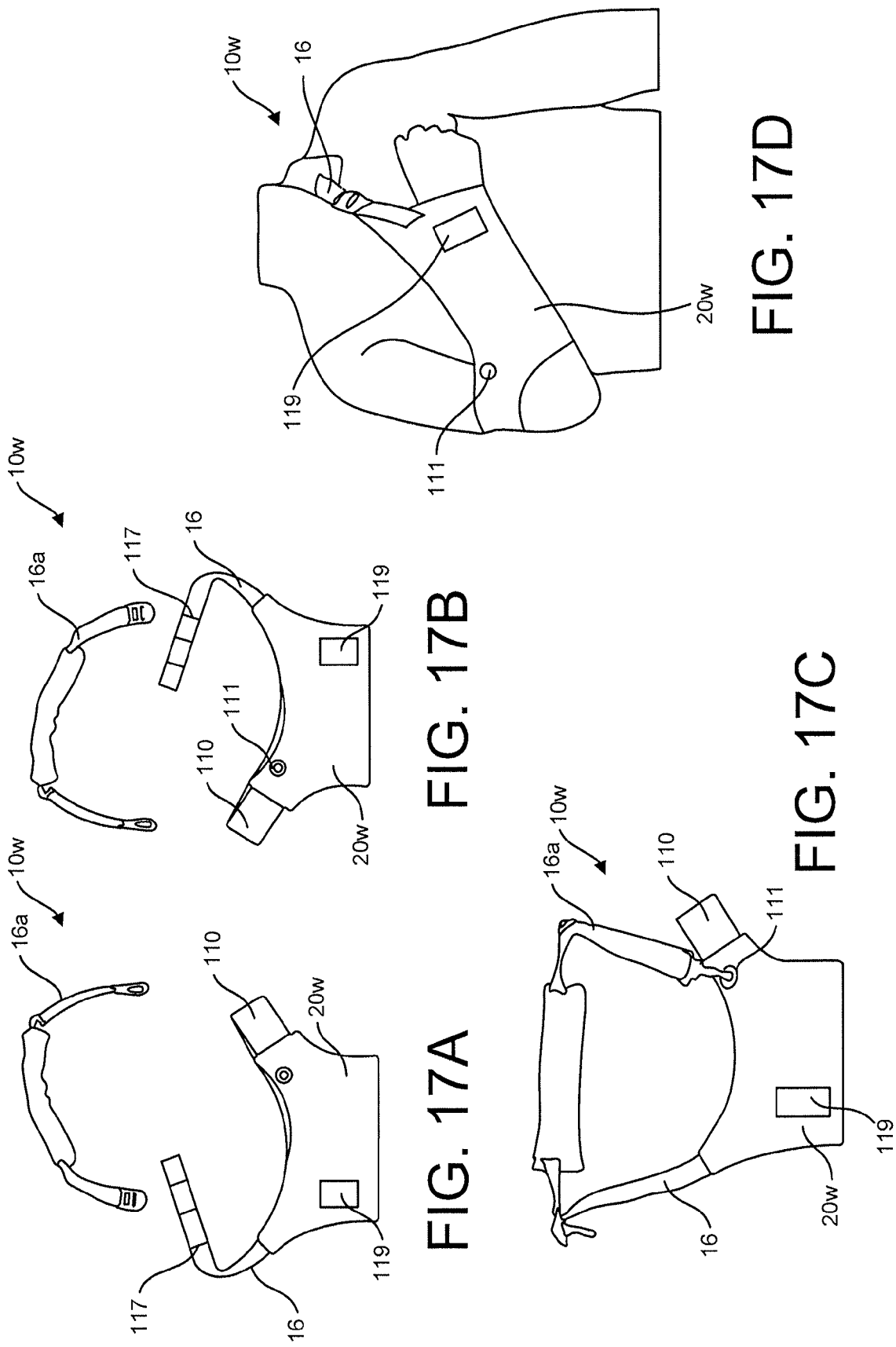

HAND ELEVATION DEVICE AND METHODS OF USE

CROSS-REFERENCE TO RELATED APPLICATIONS

This application is a national stage entry, filed under 35 U.S.C. § 371, of International Application No. PCT/US2016/046617, filed on Aug. 11, 2016, and claims the benefit of and priority to U.S. Patent Application No. 62/203,763, filed Aug. 11, 2015, the entire contents of each are incorporated herein by reference in their entireties and for all purposes.

TECHNICAL FIELD

The subject matter described herein relates to a device that supports an elevated position of a hand or wrist of a user.

BACKGROUND

Swelling is a natural physiological reaction after surgery. Reducing swelling can help speed recovery and can lessen pain experienced by the patient. For example, elevating a hand above heart level after surgery on the hand and/or associated wrist can reduce swelling of the hand and/or wrist and improve recovery.

SUMMARY

Aspects of the current subject matter can include a device that is configured to support a hand and/or wrist in an elevated position. In one aspect, the device includes a forearm support configured to support a forearm and hand of the user in a first position. The first position can include at least a part of the hand positioned above an elevation line. The elevation line can include a horizontal line that intersects a part of the heart of the user. The device can further include a neck strap that extends from the forearm support. The neck strap can be configured to extend around a part of a neck of the user and support the forearm support in the first position. In addition, the device can include an elbow strap attached to the forearm support and configured to support the forearm support relative to an upper arm of the user.

In some variations one or more of the following features can optionally be included in any feasible combination. The forearm support can include an elongated body having opposing parallel sides. The forearm support can include an elongated body having opposing sides that are angled relative to each other. The forearm support can include an elongated body having at least one first extension that extends from the elongated body at a first angle relative to a longitudinal axis of the elongated body, and the elongated body can further include at least one second extension that extends from the elongated body at a second angle relative to a longitudinal axis of the elongated body. The first angle can be within approximately 30 degrees to approximately 60 degrees. The second angle can be within approximately 110 degrees to approximately 165 degrees. The neck strap can extend between at least one of a first extension and a second extension. The elbow strap can extend between at least two second extensions. The first position can include a bend angle formed between a forearm longitudinal axis and an upper arm longitudinal axis. The bend angle can be within a range of approximately 45 degrees to approximately 80 degrees. The first position can include a position angle formed between a forearm longitudinal axis and the horizontal line. The position angle can be within a range of approximately 20 degrees to approximately 60 degrees. The first position can include an upper arm angle formed between an upper arm longitudinal axis and the horizontal line. The upper arm angle can be within a range of approximately 80 degrees to approximately 100 degrees. The neck strap can include a length adjustment feature that allows the length of the neck strap to be adjusted. The length adjustment feature can include one or more of a lanyard, a clip, a Velcro, and a pulley. The neck strap can include one or more indicators along a length of the neck strap. The forearm support can include an elongated body having a cone shape with an open end for allowing a part of an elbow of the user to extend therethrough. The device can further include at least one compartment for releasably coupling a thermal device to the forearm support. The device can further include a releasable connector that releasably connects the forearm support to the neck strap. The device can be configured for use with either the left arm or the right arm. The device can include a cushion feature that is slidably coupled to the neck strap for positioning between the neck of the user and the neck strap.

In another interrelated aspect of the current subject matter, a method includes providing a device for elevating a hand or wrist of a user with the device including a forearm support configured to support a forearm and hand of the user in a first position. The first position can include at least a part of the hand positioned above an elevation line and the elevation line can include a horizontal line that intersects a part of the heart of the user. The device can further include a neck strap that extends from the forearm support with the neck strap being configured to extend around a part of a neck of the user and support the forearm support in the first position. In addition, the device can include an elbow strap attached to the forearm support and configured to support the forearm support relative to an upper arm of the user.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIGS. 17A-17B illustrate opposing sides of an embodiment of the hand elevation device including features that allow the device to be used on either the left or right arm;

FIG. 17C illustrates the hand elevation device of FIGS. 17A-17B shown configured to be used on a right arm for supporting the user's right hand in the therapeutic position; and FIG. 17D illustrates the hand elevation device as shown in FIG. 17C being worn on a right arm of a user thereby positioning the user's hand in the therapeutic position.

When practical, similar reference numbers denote similar structures, features, or elements.

DETAILED DESCRIPTION

After a surgical procedure is performed on a patient's hand and/or wrist, a physician often instructs the patient to position the hand in a therapeutic position in order to aid in post-operative recovery of the hand and/or wrist. For example, such therapeutic position can include a part of the hand being positioned at or above the patient's heart. However, it can be common for patients to not follow such instructions and thus delay or prevent recovery. Some patients, for example, find maintaining the therapeutic position uncomfortable and leading to other issues, such as joint pain and poor circulation, which thereby results in the patient not following post-operative instructions. As such, there is a need for a device that can comfortably and effectively support a user's hand and/or wrist at the therapeutic position.

Various embodiments of a hand elevation device are described herein that comfortably and effectively support a hand and/or wrist in a position and provides therapeutic benefits after surgery of either the hand or wrist. Furthermore, the hand elevation device includes various features that assist with preventing physiological issues related to using the device, such as preventing against poor circulation and joint pain. Various other features can be included in the device, such as for further assisting with the recovery of the arm (e.g., thermal pack positioner), allowing for use with either the left or right arm, and/or adjustable features that can be manipulated with a single hand, as will be described in greater detail below.

Figure 1:
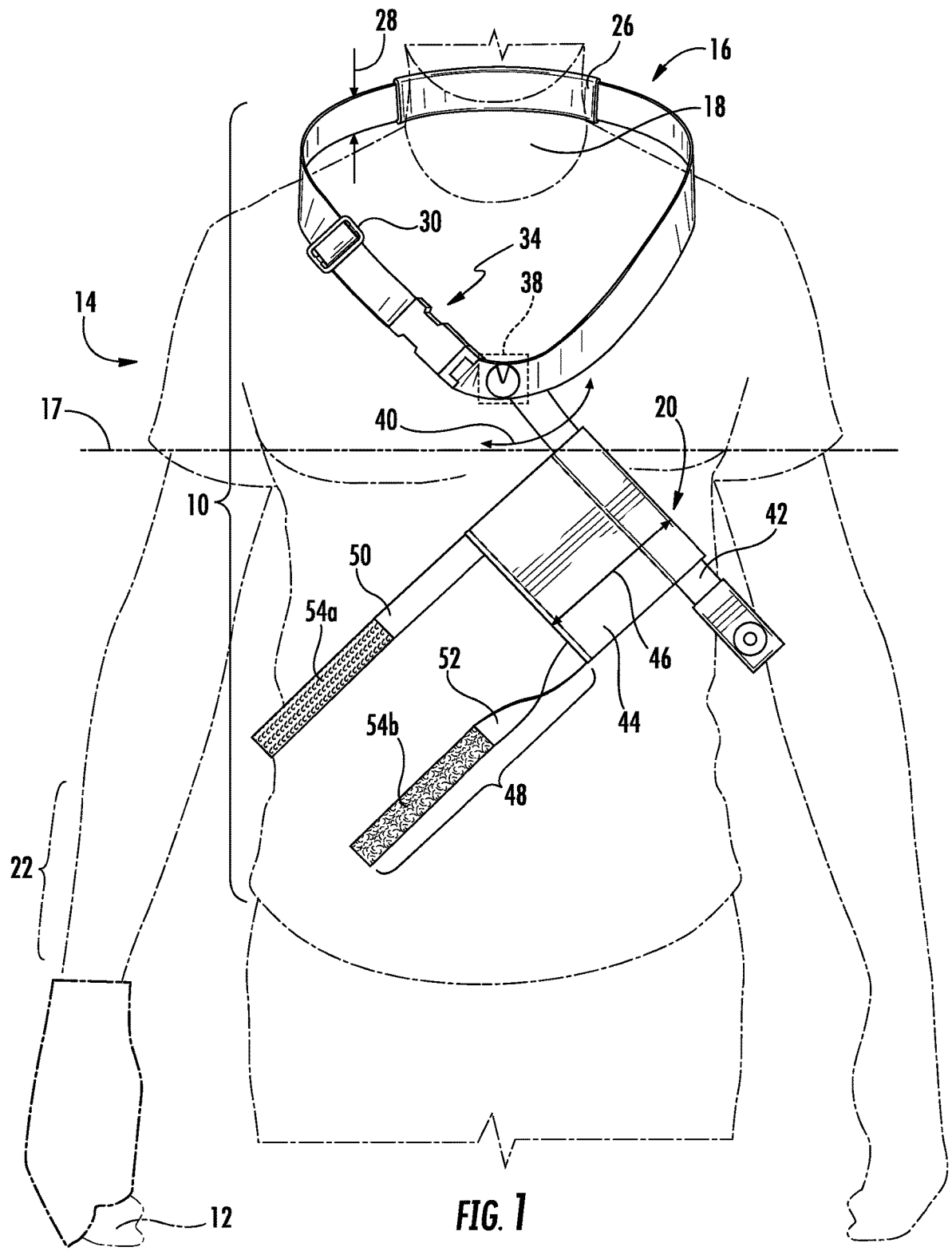
FIG. 1 illustrates an embodiment of a hand elevation device for positioning and supporting a hand of a user at or above an elevation line (a therapeutic position)
Figure 2:
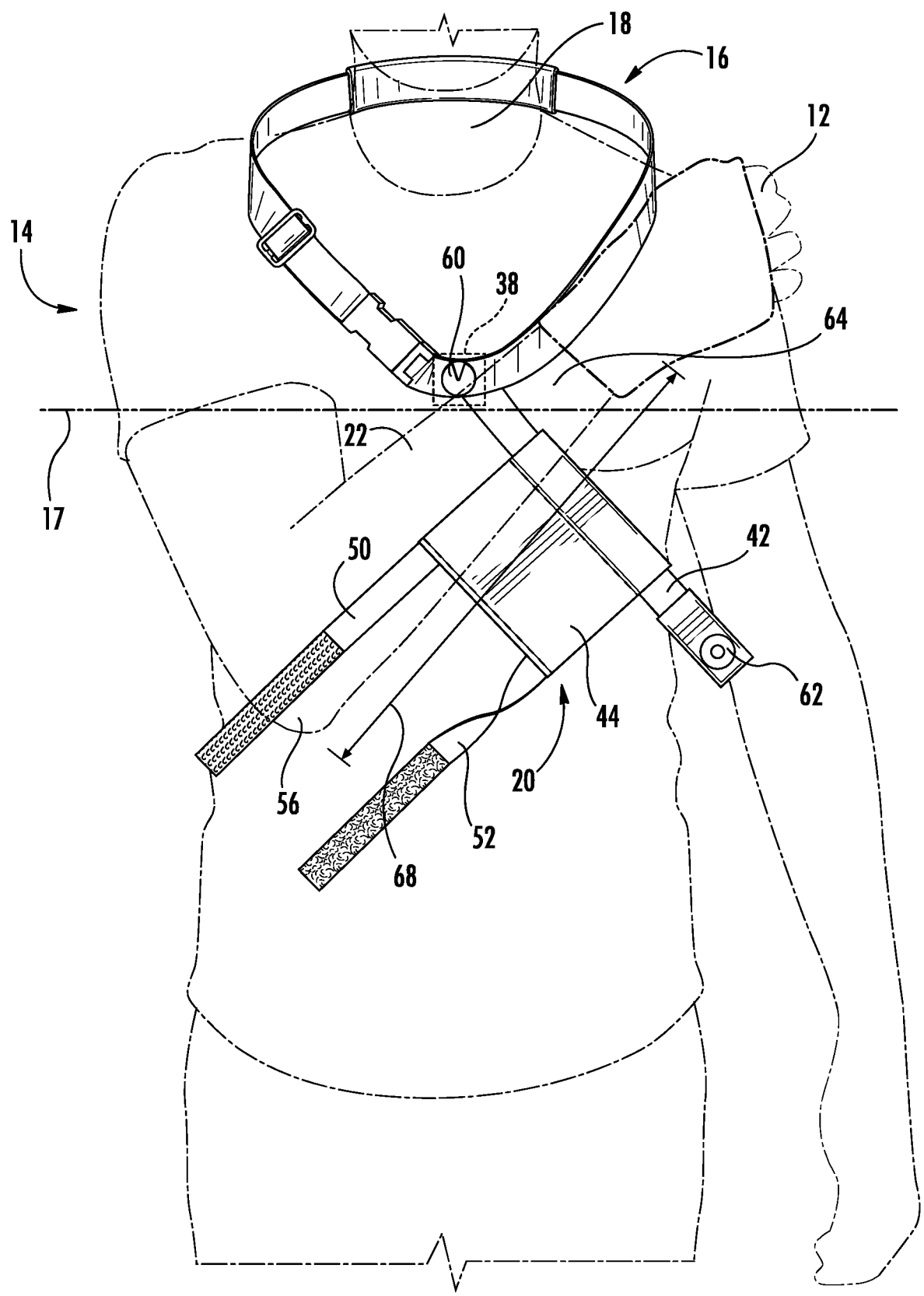
FIG. 2 illustrates the hand elevation device of FIG. 1 with the user raising a forearm so that the hand is above the elevation line in preparation for wearing the hand elevation device.
Figure 3:
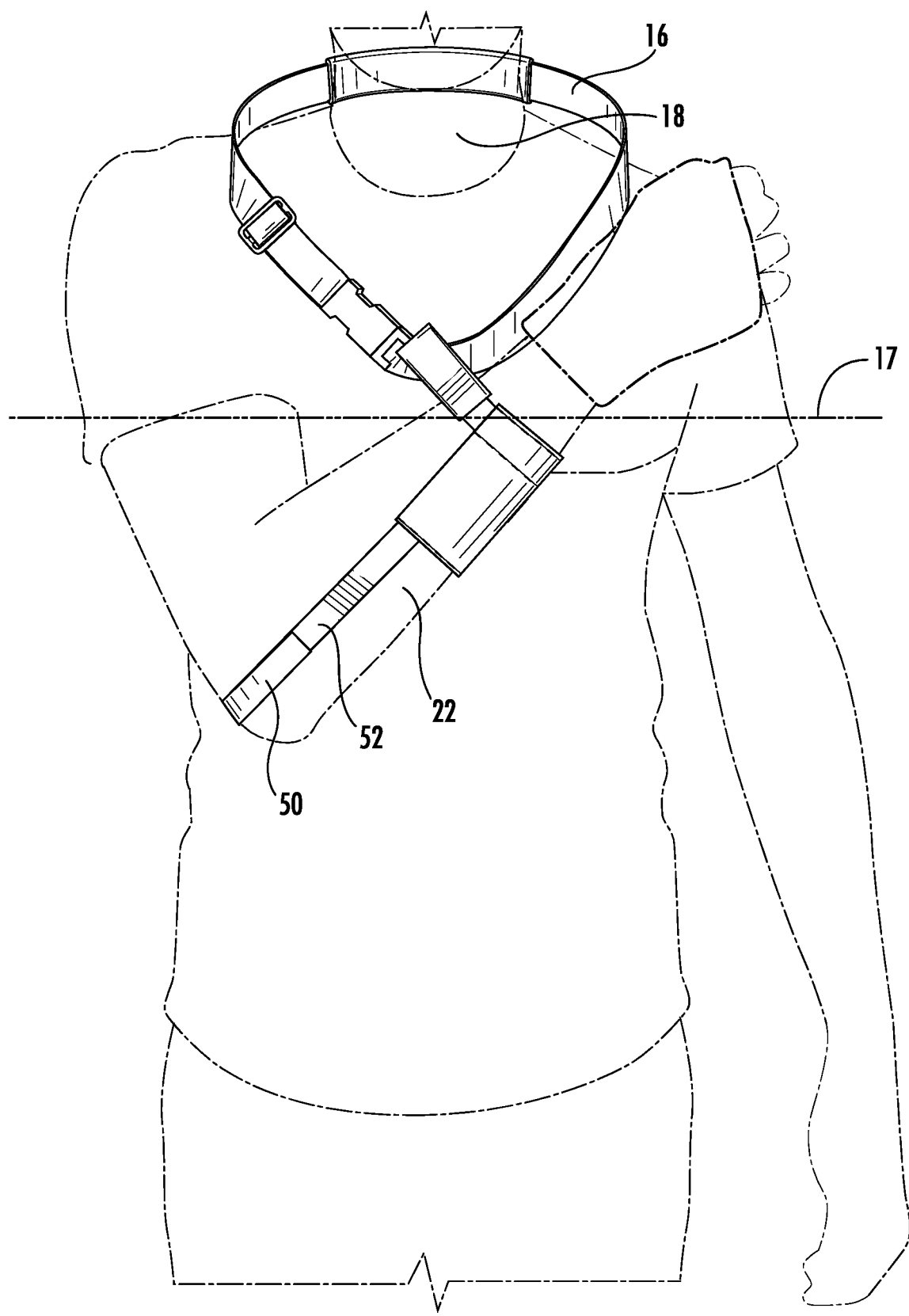
FIG. 3 illustrates the hand elevation device of FIG. 1 with the hand elevation device being worn by the user and the hand positioned above the elevation line.

FIGS. 1-4 illustrate a first embodiment of a hand elevation device 10. As shown in FIG. 3, during use, the hand elevation device 10 supports a hand 12 of a person 14 above an elevation line 17, which can reduce swelling, increase blood circulation through the hand 12, reduce edema, and mitigate pain after surgery to the hand 12 and/or associated wrist. The elevation line 17, as described herein, is defined as a horizontal line or plane that extends through the heart of the user. When any part of the user's hand is at or above the elevation line 17, the user's hand is considered to be above the elevation line 17. Such positioning of the hand 12 above the elevation line 17 is also referred to herein as the therapeutic position.

The hand elevation device 10 can include a neck strap 16 that can be worn about a neck 18 of the person 14 to allow the back of the neck to assist with supporting the positioning of the device 10, including the person's hand in the therapeutic position. The elevation device 10 can have a forearm support 20 that captures a part of the forearm 22 and assists with positioning the person's hand in the therapeutic position, including by angling the forearm, as will be discussed in greater detail below. The forearm support 20 can be attached to the neck strap 16 at one point or area so that the forearm support 20 can swivel or rotate to allow the forearm support 20 to adjust, as needed, to place the person's hand in the therapeutic position. The hand elevation device 10 is configured so that the neck 18 and forearm 22 of the person 14 can be easily inserted and removed from the hand elevation device 10 with or without the non-injured or non-operated hand.

As shown in FIG. 1, the neck strap 16 can include a cushion 26 to improve comfort and prevent the neck strap 16 from injuring or causing pain on the back side of the person's neck 18 during use of the device 10. The cushion 26 may be slidably disposed on the neck strap 16 in order to optimally position the cushion 26 at the proper location depending on the adjusted length of the neck strap 16. The cushion 26 may additionally be fabricated from various materials including but not limited to fabric, nylon, cotton, elastomeric materials, etc. Additionally, the inside surface of the cushion 26 that contacts the back side of the person's neck 18 may be lined with an anti-friction material in order to prevent slippage of the cushion 26 when the person 14 is wearing the hand elevation device 10. The cushion 26 may also be removably attached to the neck strap 16, such as for purposes of washing and replacement.

The neck strap 16 may be fabricated from various materials including but not limited to fabric, corduroy, nylon, cotton, etc., which is inelastic yet flexible/bendable. Other materials are also contemplated. The neck strap 16 can be filled with high or low density foam. The neck strap 16 can be bendable yet inelastic so that once a length of the neck strap 16 is adjusted, the position of the forearm 22 does not change regardless of how much weight is placed on the neck strap 16. This can assist with ensuring that the hand is maintained in the therapeutic position. The neck strap 16 may have a width 28 of approximately one inch. However, it is also contemplated that the width 28 of the neck strap 16 may be greater or smaller than the approximately one-inch dimension. By way of example and not limitation, the width 28 of the neck strap 16 may be up to approximately four inches wide or as small as 0.25 inches. The neck strap 16 may have an adjustable length or circumference in order to adjust a vertical position of the forearm support 20 which in turn adjusts the height of the forearm 22 and the hand 12 of the person 14. The strap 16 may have one or more buckles 30 through which the strap material 16 is threaded through in order to adjust the length of the strap 16.

Any number of features can be included in the device for adjusting the length of the neck strap, such as Velcro, snaps, buttons, etc. When the length of the neck strap 16 is increased or the circumference of the neck strap 16 increased, the forearm 22 and the hand 12 can be lowered. When the length of the strap 16 or the circumference of the neck strap 16 is decreased, the forearm 22 and the hand 12 can be raised. The length of the strap 16 can be adjusted so that the hand 12 is positioned above the elevation line 17 of the person 14 and the arm is comfortably positioned in front of the person's chest when the hand elevation device 10 is worn. In some implementations, the neck strap 16 can include one or more markers or indicators that allow the clinician to modify the neck strap 16 to prevent adjustments to the device 10 that would allow the device to be worn such that the hand was not in the therapeutic position. For example, the neck strap 16 can be modified to a length that limits the position of the forearm support 20 relative to the neck strap and/or elevation line 17 such that the hand of the user is maintained in the therapeutic position.

The neck strap 16 may also have a latch 34 that can be engaged or disengaged with one hand. The latch 34 is shown as being a side release buckle. However, other types of latches 34 are also contemplated including but not limited to pushbutton release latches, Velcro, cam lock latches, snaps, buttons, magnets, etc. The latch 34 is shown as being fully detachable. However, it is also contemplated that other types of latches may be incorporated that do not fully detach and merely allow the user to lengthen the neck strap 16 including, but not limited to tension locks, cam locks, Velcro, ladder locks, lanyards, and ladder buckles. The latch 34, when disengaged or loosened, can allow the person 14 to disconnect or lengthen the loop configuration of the neck strap 16, which can assist with putting the device 10 on or off.

In some embodiments, the forearm support 20 may be attached to the neck strap 16 at one attachment location 38 so that the forearm support 20 may pivot about the attachment location 38, as shown by pivot arrow 40 in FIG. 1. The pivot motion of the forearm support 20 can enable the hand elevation device to adjust to the physique of the person wearing the hand elevation device so that the arm is comfortably positioned in front of the person's chest and the injured or operated hand is above the elevation line 17.

Figure 8:
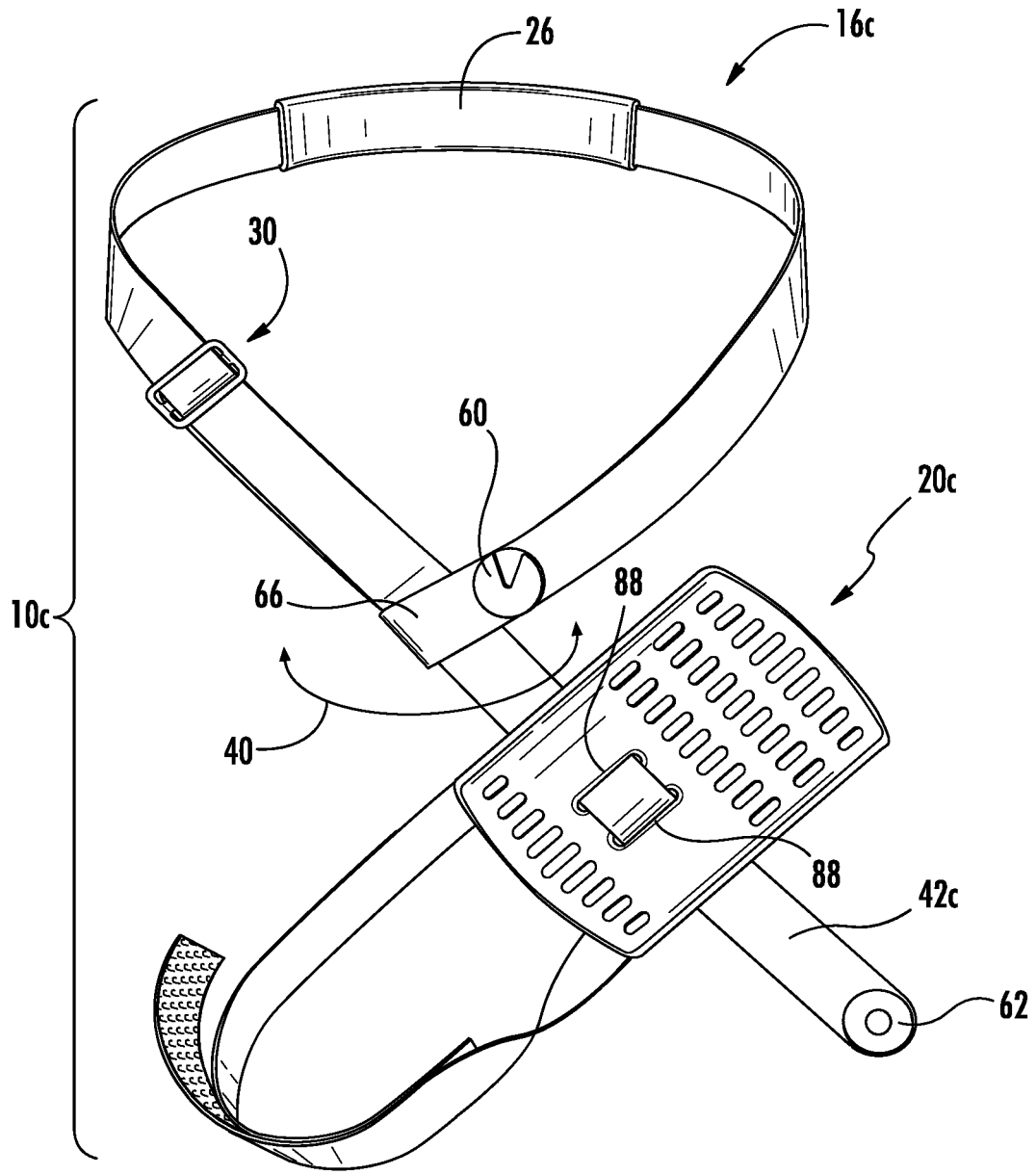
FIG. 8 illustrates another embodiment of the hand elevation device including an extended neck strap that loops around the user's neck.

The forearm support 20 may have a strap 42 that is sufficiently long to circumscribe the forearm 22 of the person 14. The strap 42 may be fixedly secured to the neck strap 16 at the attachment location 38. The strap 42 of the forearm support 20 does not shift to the left or right on the neck strap 16. Rather, the strap 42 may be sewn or otherwise secured to the neck strap 16 in order to fix the position of the strap 42 on the neck strap 16. Although the strap 42 is described as being secured to a single location 38 on the neck strap 16, it is also contemplated that the strap 42 of the forearm support 20 may be attached to the neck strap 16 at two or more locations on the neck strap 16. For example, FIG. 8 illustrates an embodiment of the forearm support 20c being attached to two different areas along the neck strap 16c. In particular, the strap 42c is connected via mating clips 60, 62 but also at location 66. As such, the forearm support 20c can pivot 40 about both the location point 66 and the mating clips 60, 62.

The forearm support 20 can include a cuff 44 that is attached to the strap 42. The cuff 44 may have a length 46 sufficiently long to comfortably support the person's forearm 22. However, the cuff 44 can also be sufficiently short in order to not overly constrain the person's arm. For example, the length 46 of the cuff 44 can be approximately three inches long to approximately 12 inches long, such as approximately six inches long. For example, the length 46 of the cuff may be sufficient to extend from a part of the forearm to at least one half the distance of the fifth metatarsal of the hand 12 of the person 14. The cuff 44 may be fabricated from soft, breathable material including but not limited to fabric and elastomeric material. Other materials are contemplated.

The cuff 44 may have an adjustable strap mechanism 48 that can be used to position the forearm support 20 relative to the forearm 22. The adjustable strap mechanism 48 may have first and second straps 50, 52. Each of the first and second straps of 50, 52 may have mating parts, such as a hooks and loops fastening system 54a, b. A first part 54a of the hooks and loops fastening system, such as the hooks, may be lined along a length of the first strap 50. The second part 54b of the hooks and loops fastening system, such as the loops, may be lined along a length of the second strap 52. The first and second parts 54a, b can be removably attachable to each other through the hooks and loops system. The length of the first and second straps 50, 52 may be adjusted and then positioned about the person's elbow 56 in order to set the exact position of the forearm support 20 on the forearm 22 of the person 14, such as to position the hand in the therapeutic position when in use. The adjustable strap mechanism may be attached to the cuff so that the first and second straps 50, 52 are disposed above and do not apply pressure to the upper epicondyle of the person's arm, thus preventing injury to the elbow joint.

The adjustable strap mechanism has been shown and described herein as being a two part strap system 50, 52. However, it is also contemplated that the adjustable strap mechanism may be a single strap that is adjustable and attachable to a side of the cuff 44 of the forearm support with a hook and loop fastening system or another fastening mechanism. As a further alternative, the adjustable strap mechanism may be two straps that are attached to each other with an adjustable buckle and/or other mechanism (e.g., snaps, etc.).

Figure 10:
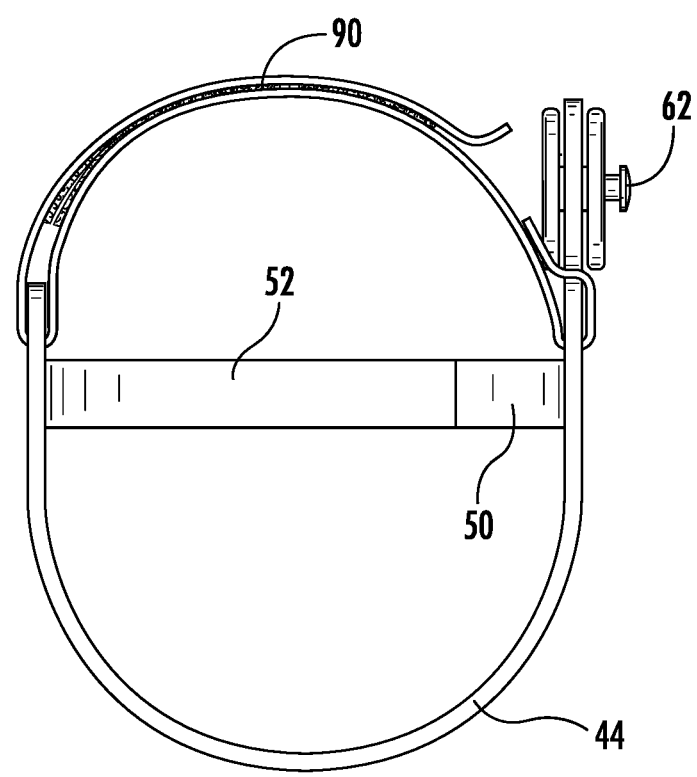
FIG. 10 is a side view of the forearm support of the hand elevation device of FIG. 9.

The forearm support 20 may also have a mating clip 62 that attaches to a clip 60 secured to the neck strap 16 (see FIG. 2). The clip 60 may have a V-shaped notch to guide the mating clip 62 into the V-shaped notch so that attachment can be made easier since the person wearing the device most likely will not have use of the injured or operated hand. The mating clip 62 is also shown in FIG. 10. Other mating approaches are also contemplated.

The hand elevation device 10 may be worn by a person whose hand 12 or associated wrist has been operated on or injured and needs to be elevated. The person may not have use of the operated or injured hand 12 or associated wrist. As such, manipulation of the hand elevation device 10 may need to be performed with one hand. The person 14 may use the non-operated or uninjured hand in order to wear and adjust the hand elevation device 10. The hand elevation device 10 may be worn or taken off with one hand 36. For example, the user may unlatch the latch 34 with one hand and place the neck strap 16 around the person's neck 18. With the neck strap 16 around the person's neck 18, the person uses the uninjured or non-operated hand 16 to reengage the latch 34.

FIG. 2 illustrates the neck strap 16 disposed about the person's neck 18. In this position, the forearm support 20 can hang below the person's neck 18 and in front of the person's chest. The person 14 can place his or her forearm 22 across his or her chest and on top of the cuff 44. The strap 42 of the cuff may be wrapped around the person's forearm 22 and engaged to the neck strap 16 by way of mating clips 60, 62. With the forearm support 20 in the proper position, the person may wrap the first and second straps 50, 52 around the person's elbow 56 and engage the hooks and loops system 54a, b. The first and second straps 50, 52 can be adjusted by the medical professional, such as to ensure the device limits the hand to be positioned in the therapeutic position. The strap 42 of the forearm support 20 can cover about one quarter or more of a distance 68 from the elbow 56 to the wrist 64. The forearm support 20 may not be positioned about the wrist but can be disposed slightly below or above the wrist 64 along the forearm 22 of the person 14. More particularly, the strap 42 of the forearm support 20 can provide the predominant supporting structure about forearm 22 and place the weight of the forearm 22 on the neck strap 16 at the attachment location 38. The first and second straps 50, 52 are disposed above or below (e.g., not on) the upper epicondyle of the person so that the elbow straps 50, 52 do not place undue pressure and cause discomfort during use.

The lengths of the neck strap 16 and the elbow straps 50, 52 may be adjusted so that the person's hand 12 is placed above the elevation line 17 of the person (in the therapeutic position). Preferably the length of the neck strap 16 and the elbow strap 50, 52 are adjusted by the medical professional. If the hand 12 is below the elevation line 17, then the length of the neck strap 16 and/or elbow strap 50, 52 can be shortened until the hand 12 is above the elevation line 17. As the hand 12 is adjusted upward, the forearm support 20 can pivot about the attachment location 38 on the neck strap 16. The pivoting of the forearm support 20 may be due to flexibility of the strap 42 or a pivoting hinge 60 (e.g., see FIGS. 9 and 10) formed between the neck strap 16 and the forearm support 20.

At times, the person may want to relax his or her arm for stretching, elbow joint extension and blood circulation. The person can use his or her uninjured or non-operated hand 36 to disengage the mating clip 62 from the clip 60 and easily remove the forearm of the operated hand 12 from the forearm support 20. FIG. 3 illustrates the hand elevation device 10 as worn on the person 14.

Figure 4:
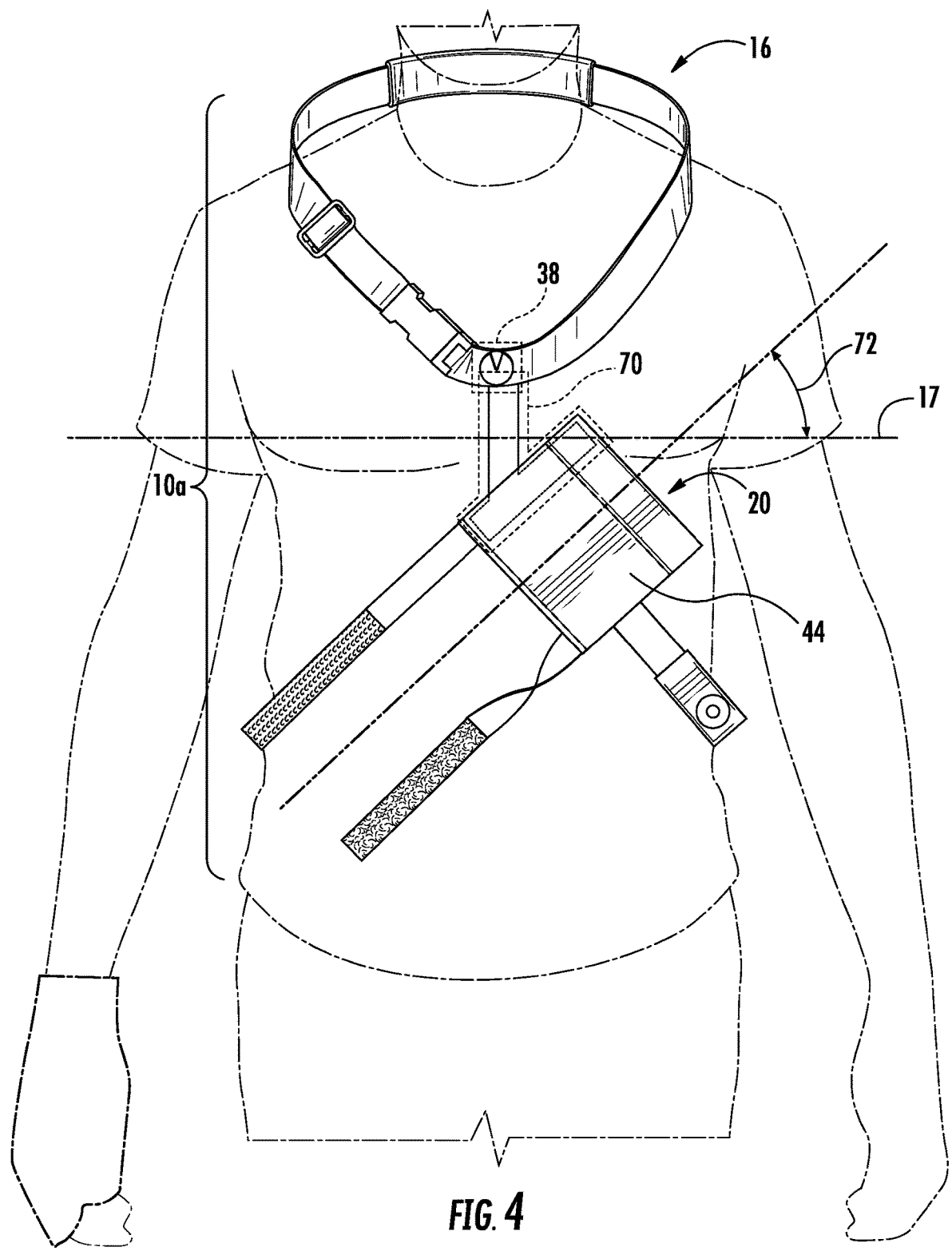
FIG. 4 illustrates another embodiment of the hand elevation device including a rigid member for supporting a forearm support of the hand elevation device at an approximate angular orientation.

Referring now to FIG. 4, the hand elevation device 10a may have a rigid member 70 that attaches the cuff 20 or forearm support 20 to the neck strap 16. The rigid member 70 can extend vertically downward from the attachment location 38 and rigidly fix to the cuff to orient the cuff 20 at an approximate angular orientation 72 with respect to the elevation line 17 thereby placing the hand in the therapeutic position when the device is in use. The rigid member 70 may be embedded within the cuff 44 to fix the angular orientation of the cuff 44 relative to the elevation line 17 or horizontal line. For example, the angular orientation can be approximately 35 degrees, or between approximately 25 degrees to approximately 45 degrees. The rigid member 70 can support the forearm of the person at the proper angular orientation so that the hand 12 of the person is raised to above the elevation line 17.

Figure 5:
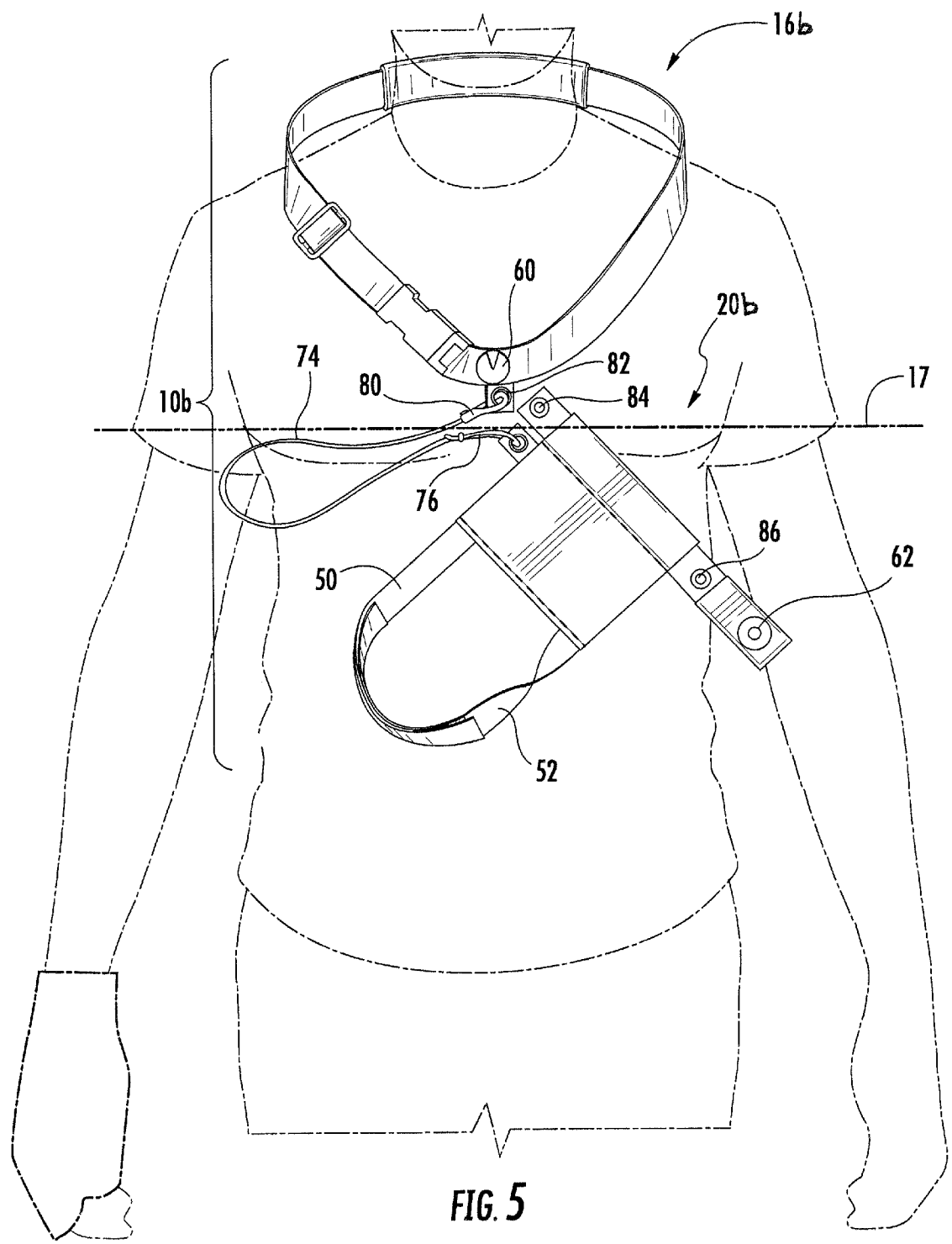
FIG. 5 illustrates another embodiment of the hand elevation device including a lanyard connecting the neck strap to the forearm support.

FIG. 5 illustrates another embodiment of the hand elevation device including a forearm support 20b that can be removably attached to the neck strap 16b and retained to the neck strap 16b with a lanyard 74. The lanyard 74 may be detachable so that the forearm support 20b can be removed completely from the neck strap 16b. For example, one end 76 of the lanyard 74 may be permanently secured to the forearm support 20b whereas the other end of the lanyard 74 may be attached to the neck strap, such as with a clip 80 that is removably attachable to a securing feature 82 extending from the neck strap 16b. The lanyard 74 is shown as being loose and not wound up. However, it is also contemplated that the lanyard 74 may be wound up in a spring-loaded case in order to prevent tangling with the user's appendages and other elements of the hand elevation device 10b. The lanyard 74 may be unwound when the neck strap 16b and the forearm support 20b need to be moved away from each other. When the forearm support 20b and the neck strap 16b are drawn closer to each other, the spring in the spring-loaded case may wind the lanyard 74 back up without any further user intervention. The forearm support 20b may be wrapped around the person's forearm and held in place by mating snaps 84, 86. Once the snaps 84, 86 are engaged to each other. The mating clips 60, 62 may be attached to each other in order to support the hand 12 of the user above the elevation line 17.

Figure 6:
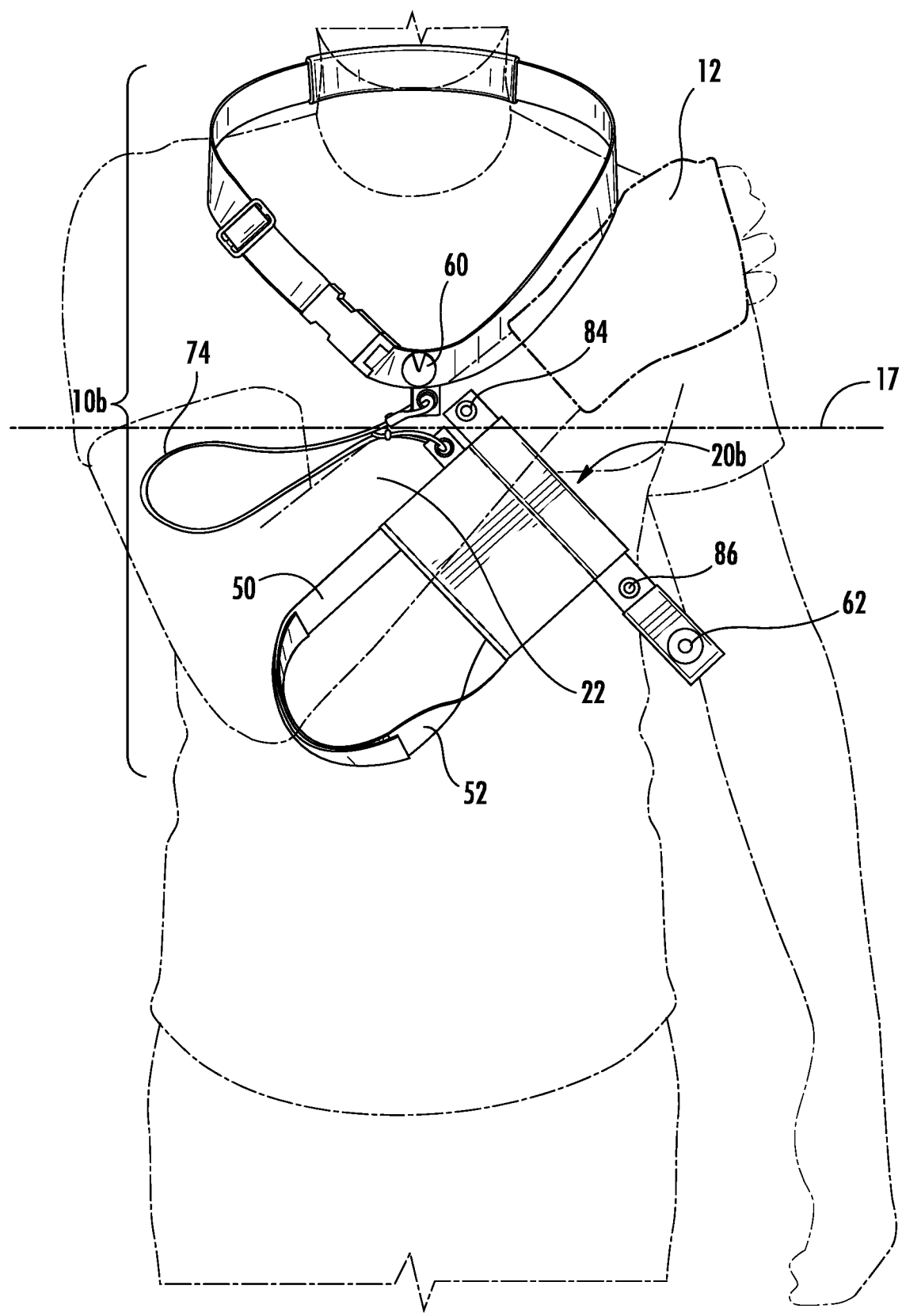
FIG. 6 illustrates the hand elevation device of FIG. 5 with the user raising a forearm so that the hand is above the elevation line in preparation for wearing the hand elevation device.
Figure 7:
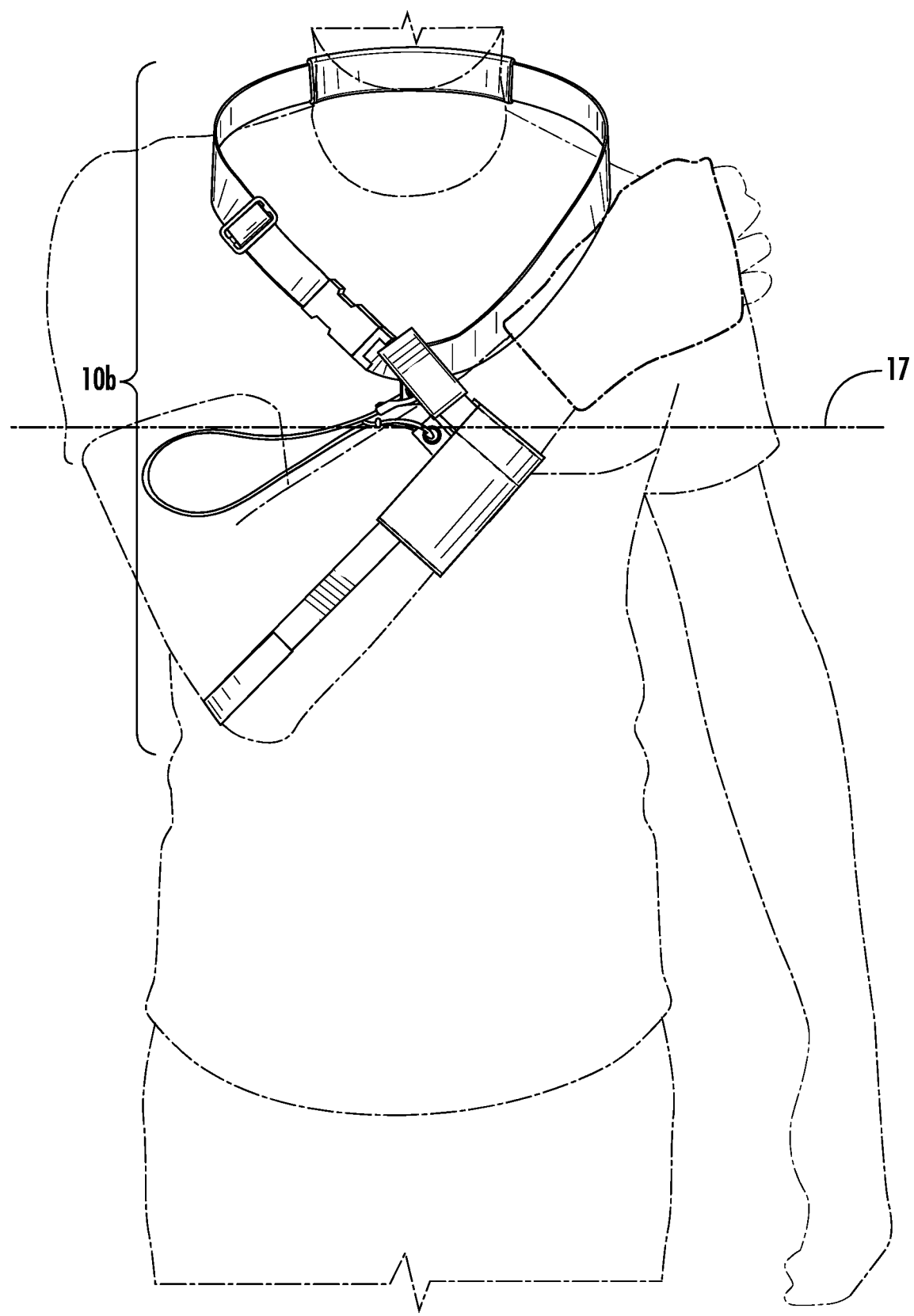
FIG. 7 illustrates the hand elevation device of FIG. 5 with the hand elevation device worn by the user and the hand positioned above the elevation line.

Referring now to FIG. 6, to wear the hand elevation device 10b, the person lifts his or her hand 12 above the elevation line 17. With the hand 12 above the elevation line 17, the user engages snaps 84, 86 about the forearm 22. The forearm support 20b is easily retrieved with the non-operated or non-injured hand since the forearm support 20b is in close proximity due to the lanyard 74. Once the mating snaps 84, 86 are engaged to each other, the mating clips 60, 62 can be attached to each other thereby completing the install or wearing of the hand elevation device 10b on the person. FIG. 7 illustrates the hand elevation device 10b as worn on the person with the hand in the therapeutic position (e.g., at least a part of the hand is above the elevation line 17).

Referring now to FIG. 8, another embodiment of the hand elevation device 10c is shown. The hand elevation device 10c integrates an extension 42c to the neck strap 16c such that the neck strap 16c and the extension 42c may be fabricated from one elongate length of material. The neck strap 16c may have a loop at location 66 (e.g., a distal end) through which the extension is fed through in order to provide a loop configuration so that the neck strap 16c can be hung around the person's neck. In order to prevent the strap from closing in on the person's neck, the strap 16c can be sewn at location 66 to prevent a fixed attachment between the location 66 on the strap 16c itself. The circumference or length of the neck strap 16c may be adjusted via a buckle 30. The length of the neck strap 16c can also be adjusted by providing a plurality of attachment points along the length of the strap 16c. The location 66 may have a mating attachment mechanism that can be removably attachable to any one of the plurality of attachment points 60, 62. This can provide for adjustability in the length of the neck strap 16c as well as fixation of the location point 66 along the strap 16c to allow the forearm support 20c to pivot through an angle 40 and prevent the neck strap 16c from closing down on the person's neck during use.

In some implementations, the forearm support 20c may be fabricated from a bendable plastic material that is comfortable when worn by the patient. The forearm support 20c may have one or more apertures 88 through which the strap or extension is looped through in order to adjust the position of the forearm support 20c on the strap 16c.

Figure 9:
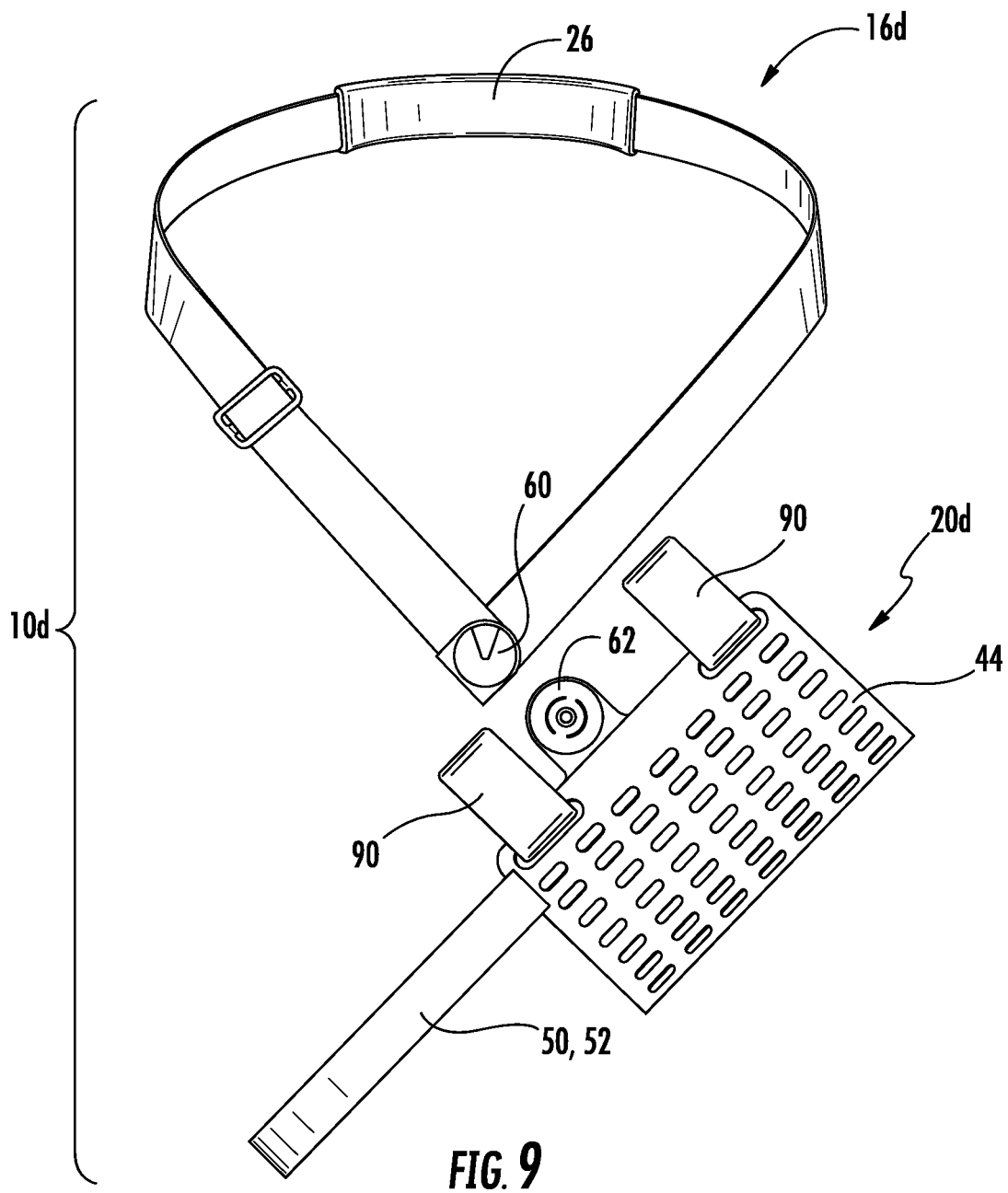
FIG. 9 illustrates another embodiment of the hand elevation device including a connector that releasably attaches the forearm support to the neck strap.

Referring now to FIGS. 9 and 10, another embodiment of the hand elevation device 10d is shown. The forearm support 20d can be removably attachable to the neck strap 16d by way of mating clips 60, 62. The neck strap 16d and forearm support 20d may be retained together with the lanyard 74, as discussed above. The circumference of the forearm support 20d may be secured around the forearm with hook and loop straps 90 and/or other attachment features, such as buckles, buttons, snaps, etc. Straps 90 may be pulled closer until the cuff 44 is securely wrapped around the person's forearm 22. The forearm support 20d may have first and second straps 50, 52 as discussed above. The hand elevation device 10d allows the forearm support 20d to pivot about a single point defined by the mating clips 60, 62. The clip 60 may have a V-shaped notch in which the mating clip 62 fits within. The mating clip 62 has an enlarged nub that fits behind the V-shaped notch so that the mating clip 62 is retained on the clip 60. The V-shaped notch also guides the mating clip 62 into the V-shaped notch in order to assist the person in engaging the forearm support 20d to the neck strap 16d. Other mating systems are contemplated and can be included in the hand elevation device 10d.

Figure 11A:
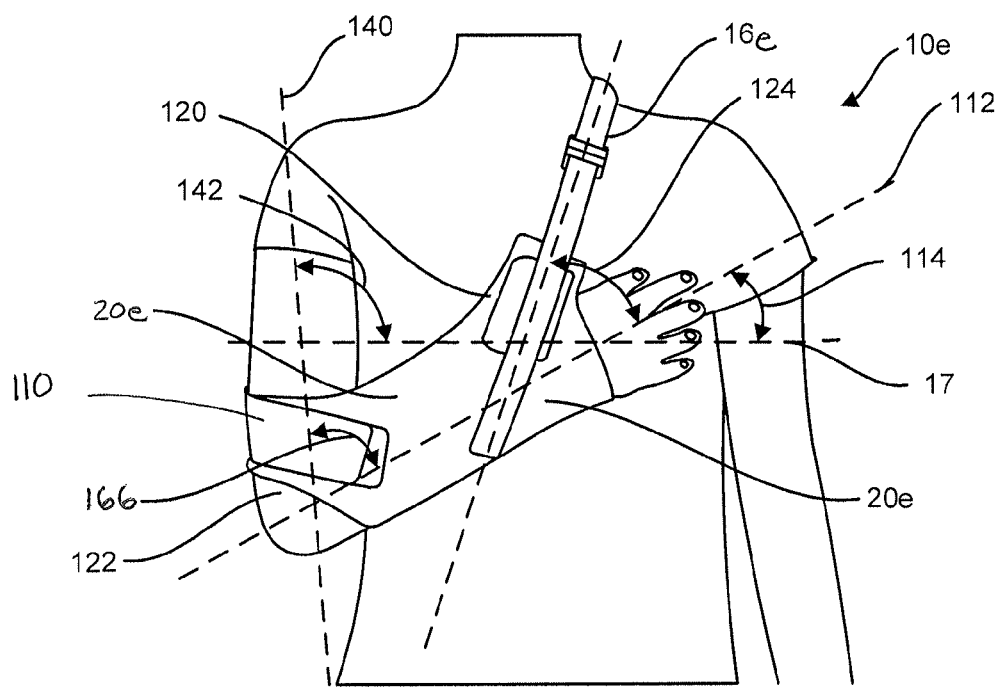
FIG. 11A illustrates a front view of another embodiment of the hand elevation device including a neck strap and an elbow strap.
Figures 11B, 11C:
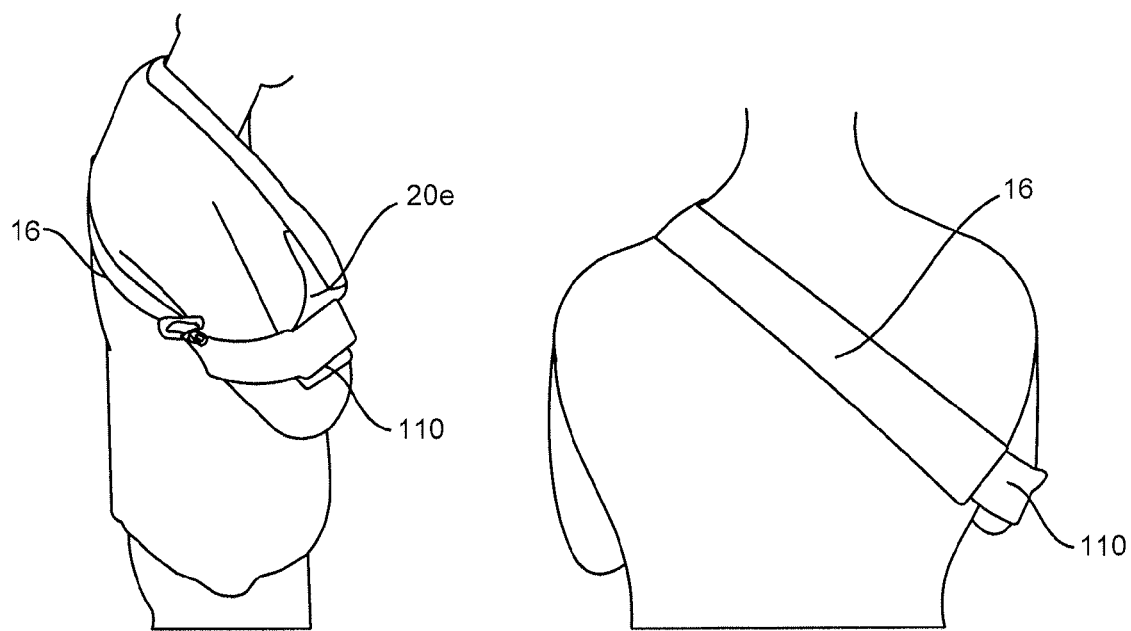
FIG. 11B illustrates a side view of the hand elevation device of FIG. 11A.
FIG. 11C illustrates a back view of the hand elevation device of FIG. 11A.

FIGS. 11A-11C show another implementation of the hand elevation device 10e that includes a forearm support 20e, a neck strap 16e, and an elbow strap 110, which can include any of the features and functions described above. Similar to the above embodiments of the device, the hand elevation device 10e shown in FIGS. 11A-11C is configured to beneficially position a post-surgery or recovering hand and/or wrist in the therapeutic position in order to reduce swelling and improve recovery of the arm. When adjusting the hand elevation device 10e to ensure the hand is in the therapeutic position, for example, a line extending between left and right nipples of the user can be used as an approximate guide to where the elevation line 17 is located.

The therapeutic position can also be defined herein by a first angle 114 formed between a horizontal axis, such as the elevation line 17, and a longitudinal axis 112 extending along the forearm or forearm support 20e, as shown in FIG. 11A. The first angle 114 can range between approximately 20 degrees and approximately 60 degrees, such as approximately 45 degrees. The longitudinal axis 112 of the forearm support 20e can be approximately parallel to a longitudinal axis of the forearm captured within forearm support 20e. Additionally, the therapeutic position can further include positioning the forearm and hand of the recovering arm in alignment with each other with the palm of the hand facing the chest of the user. Furthermore, the therapeutic position can include positioning the upper arm (or upper arm longitudinal axis 140) of the recovering arm such that it is approximately perpendicular to a horizontal axis (or the elevation line 17), such as when looking at the upper arm from a front view, as in FIG. 11A. For example, the therapeutic position can include the upper arm longitudinal axis 140 forming a second angle 142 relative to the elevation line 17, where the second angle 142 can have a range of approximately 80 degrees to approximately 100 degrees, such as 90 degrees. The therapeutic position can further include the upper arm longitudinal axis 140 forming a bend angle 166 relative to the longitudinal axis 112 of the forearm or support 20e, where the bend angle 166 can have a range of approximately 45 degrees to approximately 80 degrees. The hand elevation device 10e can assist with situating and maintaining the recovering arm in the therapeutic position, which can improve recovery as well as provide comfort to the user while wearing the hand elevation device 10e.

As shown in FIG. 11A, the forearm support 20e can have an elongated body that supports the user's forearm and wrist during use. A part of the user's hand can also be supported by the forearm support 20e. For example, the forearm support 20e can extend from a point approximately half way along the fifth metatarsal of the hand to a distance along the forearm, such as adjacent the elbow. The forearm support 20e can be configured such that the elbow of the recovering arm is exposed when the user is wearing the hand elevation device 10e, as shown in FIGS. 11A-11B. By exposing the elbow, comfort to the user can be improved, as well as preventing any irritation or damage to the elbow area due to the elbow pressing down onto the forearm support 20e over an extended period of time.

Figure 11D:
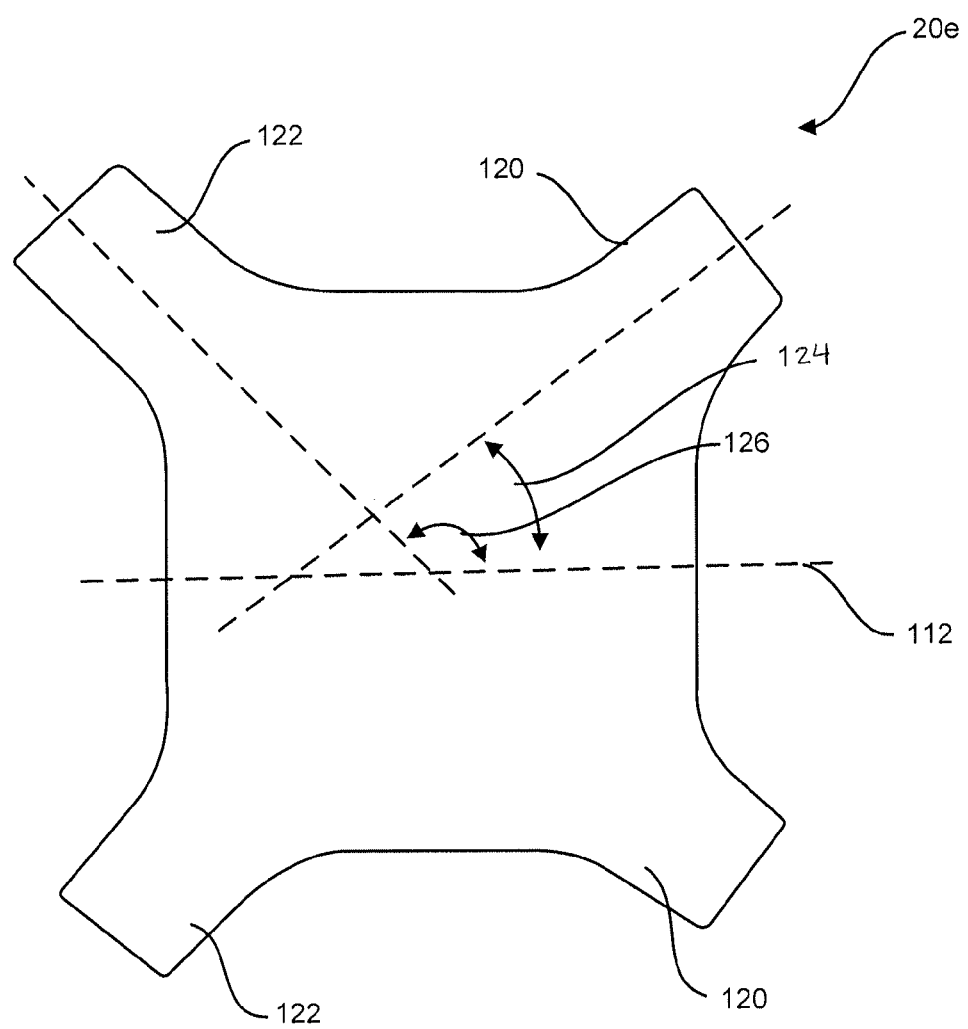
FIG. 11D illustrates an implementation of the forearm support laid out in a flat configuration, such as before assembly to the neck strap and elbow strap.

FIG. 11D shows an implementation of the forearm support 20e laid out in a flat configuration, such as before assembly to the neck strap 16e and elbow strap 110. As shown in FIG. 11D, the forearm support 20e can include first extensions 120 and second extensions 122 that assist with securing the recovering arm in the therapeutic position. For example, each of the first extensions 120 can extend from the elongated body of the forearm support 20e at a first extension angle 124 relative to the longitudinal axis 112 of the forearm support 20e. In addition, each of the second extensions 122 can extend from the elongated body of the forearm support 20e at a second extension angle 126 relative to the longitudinal axis 112. The first extension angle 124 can include a range between approximately 30 degrees to approximately 60 degrees, such as approximately 45 degrees. The second extension angle 126 can include a range between approximately 110 degrees to approximately 165 degrees, such as approximately 135 degrees.

The neck strap 16e, which can have a first and second end, can attach to one or both of the first extensions 120 at the first end and attach to either another first extension 120 or one or both of the second extensions 122 at the second end. In some implementations, when the neck strap 16e is properly fitted and extends around one side of the user's neck and diagonally across the user's back (as shown in FIGS. 11A-11C), the neck strap 16e can extend from the forearm support 20e at approximately the first extension angle 124 from the first extension(s) 120 and at the second extension angle 126 from the second extension(s) 122. This can assist with securing the recovering arm in the therapeutic position, which includes positioning the hand above the elevation line 17 and positioning the forearm at the first angle 114, as shown in FIG. 11A.

The elbow strap 110 can extend between one or more sides of the forearm support 20e and support a part of the upper arm of the user, as shown in FIGS. 11A and 11B. For example, the elbow strap 110 can extend between the second extensions 122 of the forearm support 20e. This can allow the elbow strap to form a U-shape that extends around and conforms to a part of the upper arm of the user. In such a configuration, the elbow area remains exposed and does not experience pressure exerted by either the elbow strap or the forearm support 20e. In some implementations, the neck strap 16e can couple to a part of the elbow strap 110.

Any part of the hand elevation device 10e can be adjusted and/or in order to provide the user with a correct fit such that the hand elevation device 10e can stabilizes and maintains the hand of the user in the therapeutic position. For example, the neck strap 16e can be adjustable to allow the user to lengthen and shorten the neck strap 16e, such as for taking the hand elevation device 10e on and off. In some implementations, the neck strap 16e can be modified, such as by a physician, in order to limit the number of variations the hand elevation device 10e can be worn. For example, the neck strap 16e can be adjusted to a desired length that positions the recovering arm in the therapeutic position. Once the neck strap 16e has been adjusted to a desired length, at least a portion of the excess neck strap can be removed thereby preventing the hand elevation device 10e from being worn where the neck strap 16e is not at the desired length and thus not positioning the recovering arm in the therapeutic position.

In some implementations, the elbow strap 110 can be adjustable and/or modifiable in order to provide the user with a customized and correct fit. For example, the elbow strap 110 can include a Velcro strap that can be removably secured to the forearm support 20e. Similar to as described above with respect to the neck strap 16e, the elbow strap 110 can be modified, such as by a physician, in order to limit the number of variations the hand elevation device 10e can be worn. For example, once the elbow strap 110 has been adjusted to a desired length that positions the recovering arm in the beneficial position, at least a portion of the excess elbow strap 110 can be removed, thereby limiting the adjustability of the elbow strap 110. As such, the hand elevation device 10e can be configured to be adjustable within a range that allows the user to take the device on and off, as well as make minor adjustments that still allow the user to wear the hand elevation device 10e such that it positions the recovering arm in the therapeutic position.

The elbow strap 110 and/or neck strap 16e can be adjustable and/or modifiable in a variety of ways. For example, one or more of a variety of features can be used to allow the elbow strap 110 and/or neck strap 16e to be adjusted and/or modified. Some features can include, for example, Velcro, button snaps, pulley features, draw strings, buckles, etc. In some implementations, either the elbow strap 110 or neck strap 16e can include visual ques (e.g., markings, physical features, etc.) that assist the user with properly adjusting the elbow strap 110 or neck strap 16e such that the hand elevation device 10e positions the recovering arm in the therapeutic position.

The neck strap 16e may be made out of a fabric or webbed material, which can have elastic properties. The neck strap 16e may also be padded with low or high-density foam or other material. The neck strap 16e can connect from the elbow strap 110 and extend around the contralateral shoulder. The neck strap 16e may be adjustable using Velcro, notches, mechanical or other means. Adjustable length of the neck strap 16e can be between approximately 18 inches and approximately 36 inches, such as approximately 24 inches. The width of the neck strap 16e can either be consistent across its entire length or taper, such as from a narrower width to a wider width. The width of the neck strap 16e may vary between approximately 0.5 inch and approximately 4 inches. For example, the width of the neck strap 16e can be approximately 1 inch at the point of connection to the forearm support 20e and taper to approximately 3 inches at the shoulder, then remaining consistent to its terminal point on the elbow strap 110.

The neck strap 16e that extends diagonally across the back similar to a messenger bag (as shown in FIG. 11C), which can assist with allowing the back and shoulder of the user to bear at least some of the weight of the recovering arm and keeping at least some of the force off of the user's neck. By shortening the neck strap 16, the hand can be positioned closer toward the shoulder. Conversely, by lengthening the neck strap 16 the hand can be lowered toward parallel and/or closer to the ground. In some implementations, when the elbow strap 110 is horizontal (or parallel to the user's waistline, ground, or elevation line 17), the elbow strap 110 is considered to be in a correct position thereby assisting with positioning the recovering hand in the therapeutic position. The ability to adjust the hand elevation device 10e can allow individuals of varying sizes to comfortably use and benefit from use of the device, including for either left or right hand use.

The elbow strap 110 can be made out of a fabric or webbed material, and can connect the forearm support 20e to the neck strap 16e. The elbow strap 110 may be made from materials that exhibit varying degrees of elasticity or no elasticity. The elbow strap 110 may be adjustable via Velcro, buckle, snaps, mechanical clasps or other means. The elbow strap 110 may measure anywhere from approximately 2 inches to approximately 10 inches, such as approximately 5 inches. The elbow strap 110 may contain mechanical connection points for the neck strap 16e. In some embodiments, the neck strap 16e is sewn directly to the elbow strap 110 creating a left or right arm sling (i.e., not ambidextrous). In another embodiment, the neck strap 16e is sewn in a loop around the elbow strap 110 and allows for the user to set the neck strap 16e laterality by sliding the loop along the elbow strap 110. In another embodiment, the neck strap 16 attaches to the elbow strap 110 via a mechanical attachment device such as snap fasteners that allow the hand elevation device 10e to be set for either left or right hand use.

The elbow strap 110 can assist with keeping the upper part of the recovering arm positioned alongside the torso, such as creating an approximate 90 degree angle to the floor, as shown in FIG. 11A. The elbow strap 110 can also provide a visual cue that the hand elevation device 10e is adjusted properly and that the arm is the therapeutic position. For example, when adjusted properly, the elbow strap 110 can extend approximately parallel to the ground (or horizontal). The elbow strap 110 combined with the forearm support 20e can create a pocket that encompasses the elbow. The elbow pocket can allow the elbow to rest comfortably while repositioning a portion of the weight off of the shoulder and neck and onto the Trapezius and Deltoid muscles. This can provide for greater comfort and less fatigue for the user. The elbow strap 110 can be positioned in relation to the forearm support 20e such that the material of the elbow strap 110 sits above the epicondyle nerve of the user to reduce the likelihood of impingement of the epicondyle or ulnar nerve.

The forearm support can be made out of any number of fabrics and/or materials. The material that the forearm support is made from can exhibit varying degrees of elasticity or no elasticity.

Figure 12:
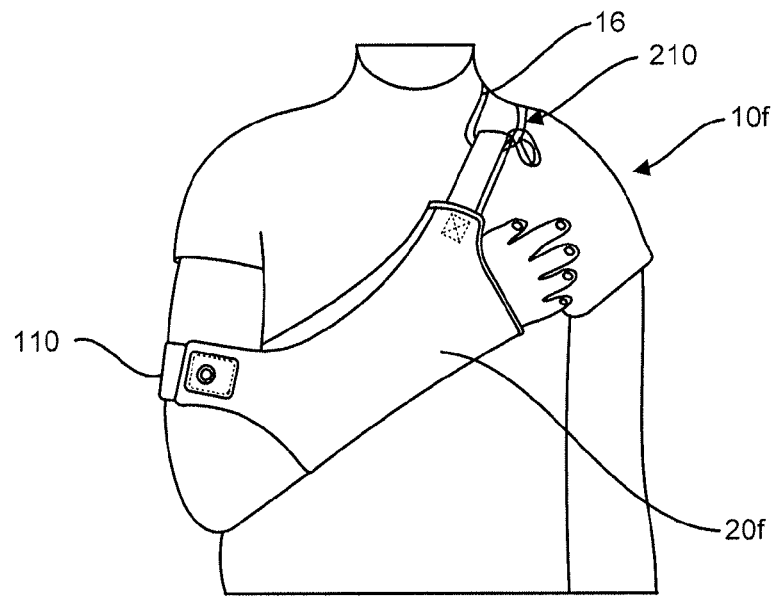
FIG. 12 illustrates a front view of another embodiment of the hand elevation device including a neck strap having a pulley support.

FIG. 12 illustrates another implementation of the hand elevation device 10f that includes an adjustable pulley support 210 that can assist with positioning the hand relative to the elevation line 17. The pulley support 210 can be made out of one or more of a fabric, elastic cord, mesh, webbing or other material. In some embodiments, the pulley support 210 is constructed of elastic cord. The pulley support 210 can be connected to the neck strap 16 and/or forearm support 20f by a sewn connection, however, any number of mechanical connections can be used, such as snaps, hooks, Velcro, etc. Furthermore, the pulley support 210 can be adjusted by any number of mechanical features, such as Velcro, push-button, hook and loop, or other adjustable features.

The pulley support 210 can assist with changing (i.e., increasing or decreasing) the distance between the neck strap 16 and the forearm support 20f. This can assist with adjusting the hand elevation device 10f, as well as assisting with taking the hand elevation device 10f on and off without changing the fitted lengths of the neck strap 16 or elbow strap 110. In addition, the pulley support 210 can include an open position that allows the user to easily take the hand elevation device 10f on and off. The pulley support 210 can also include a closed position that secures the hand elevation device 10f in the therapeutic position and limits movement of the recovering arm. In some implementations, a free end of the pulley support 210 can be pulled, such as by a single hand of the user, in order to adjust the pulley support into the open position or closed position. Thus, the pulley support 210 can provide for single handed positioning and adjustment of the hand elevation device 10f.

In some implementations, a part of the pulley support 210 can be releasably secured to a part of the hand elevation device in order to fix the positioning of the pulley support 210, such as in a prescribed position or configuration. For example, the hand elevation device 10f can include a patch of Velcro that a part of the pulley support 210 can releasably secure to for securing the pulley support 210 and, in turn, the forearm support 20f in the therapeutic position. The pulley support 210 can also allow for the hand elevation device 10f to be easily adaptable for supporting and stabilizing either the user's left or right hand and/or wrist. A variety of features can be included with the hand elevation device 10f for securing the pulley support 210 to the forearm support 210 and preventing unwanted uncoupling therebetween.

Figures 13A, 13B:
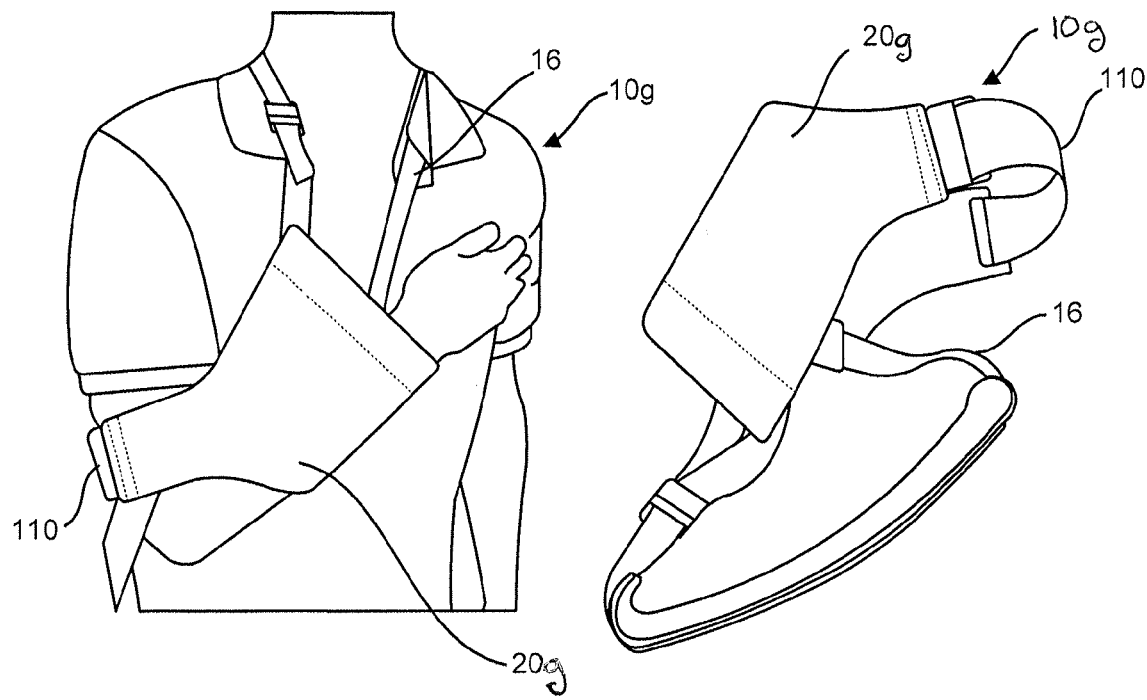
FIG. 13A illustrates a front view of another embodiment of the hand elevation device including a neck strap and an elbow strap.
FIG. 13B illustrates a top view of the hand elevation device of FIG. 13A not being worn by a user.

FIGS. 13A and 13B illustrate another implementation of the hand elevation device 10g including a forearm support 20g having a neck strap 16 that extends between opposing sides of a first end of the forearm support 20g. The neck strap 16 can be worn such that the neck strap 16 loops around the back side of the user's neck, as shown in FIG. 13A. The neck strap 16 can include an adjustment feature (e.g., a buckle, snaps, Velcro, etc.) that allows the neck strap 16 to be extended and shortened.

As shown in FIGS. 13A and 13B, the hand elevation device 10g can also include an elbow strap 110 that extends between opposing sides of a second end of the forearm support 20g. In addition, the second end can include an extension that positions the elbow strap 110 approximately parallel to the floor when the hand elevation device 10g is properly worn by the user, as shown in FIG. 13A. The elbow strap 110 can include an adjustment feature that allows the elbow strap 110 to be extended and shortened. Similar to as described above, either the elbow strap 110 or neck strap 16 can be modified such that they limit the adjustability of the hand elevation device 10g so that the device maintains the recovering arm of the user in the therapeutic position.

Figure 14A:
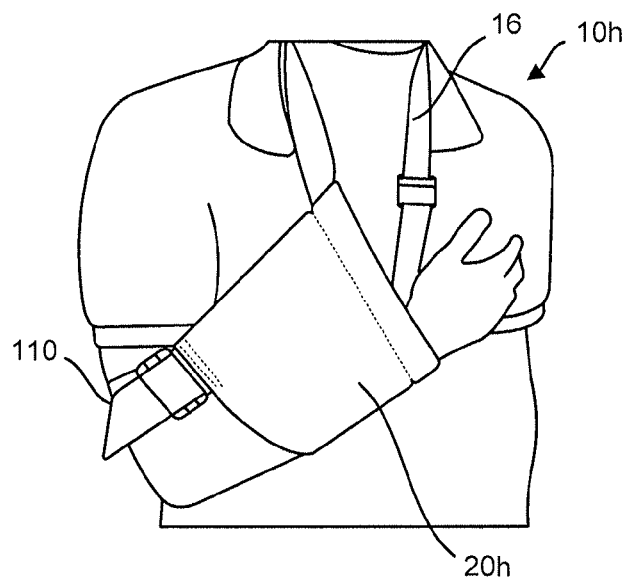
FIG. 14A illustrates a front view of another embodiment of the hand elevation device being worn by a user.
Figure 14B:
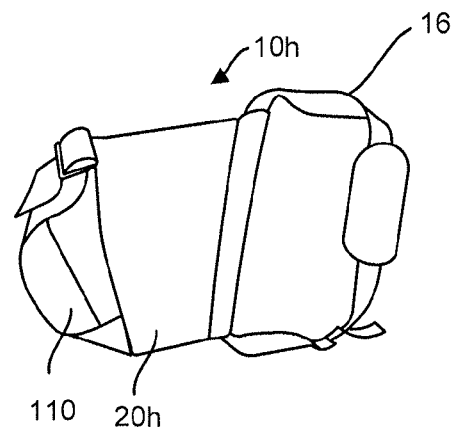
FIG. 14B illustrates a top view of the hand elevation device of FIG. 14A not being worn by a user.
Figure 15A:
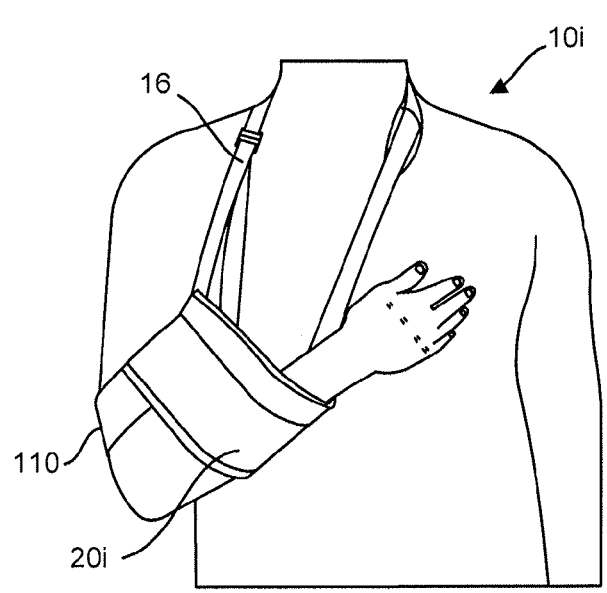
FIG. 15A illustrates a front view of another embodiment of the hand elevation device including a neck strap and an elbow strap.
Figure 15B:
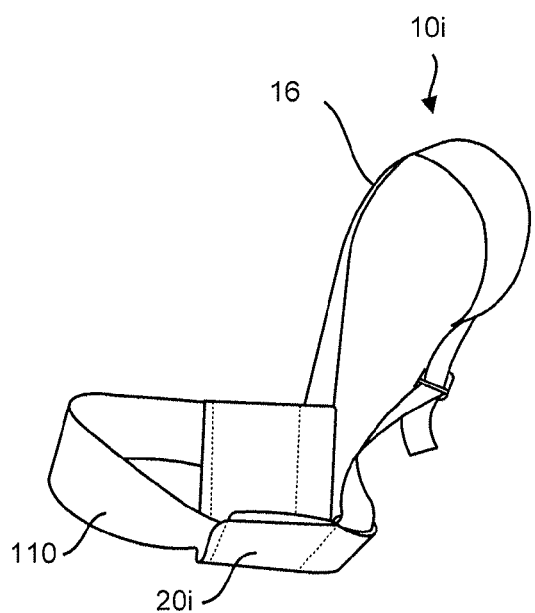
FIG. 15B illustrates a top view of the hand elevation device of FIG. 15A not being worn by a user.

The forearm support can have a variety of shapes and sizes, which can assist with securing the recovering arm in the therapeutic position. As shown in FIGS. 14A-14B, for example, the forearm support 20h of the hand elevation device 10h can include opposing angled sides (as shown in FIG. 14B) with the neck strap 16 extending from a first end, and the elbow strap 110 extending from a second end. In some implementations, the forearm support can include one or more opposing sides that are parallel to each other, such the hand elevation device 10i shown in FIGS. 15A and 15B. As also shown in FIGS. 15A and 15B, the neck strap 16 can extend from a first end of the forearm support 20i and the elbow strap can extend from a second end of the forearm support 20i.

In some implementations of the hand elevation device, such as hand elevation device 10g and 10h (see FIGS. 13A-13B and 14A-14B, respectively), the asymmetrical shape of the forearm support can assist with allowing the neck strap 16 to extend tangent to the sides of the user's neck when the user is wearing the hand elevation device in the therapeutic position. For example, a side of the forearm support that engages the neck strap 16 can be angled to allow for the neck strap 16 to extend tangent to the sides of the user's neck when the hand elevation device is being worn in the therapeutic position.

Figure 16A:
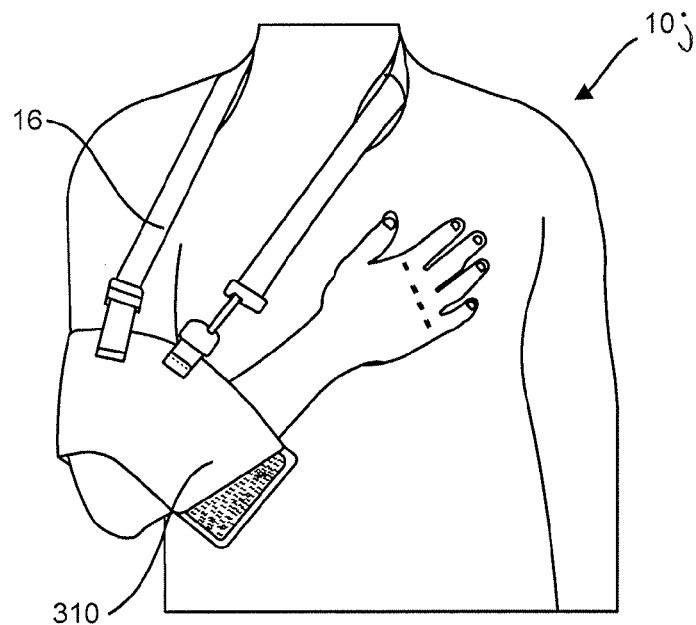
FIG. 16A illustrates a front view of another embodiment of the hand elevation device including a neck strap, arm sleeve, and elbow strap.
Figure 16B:
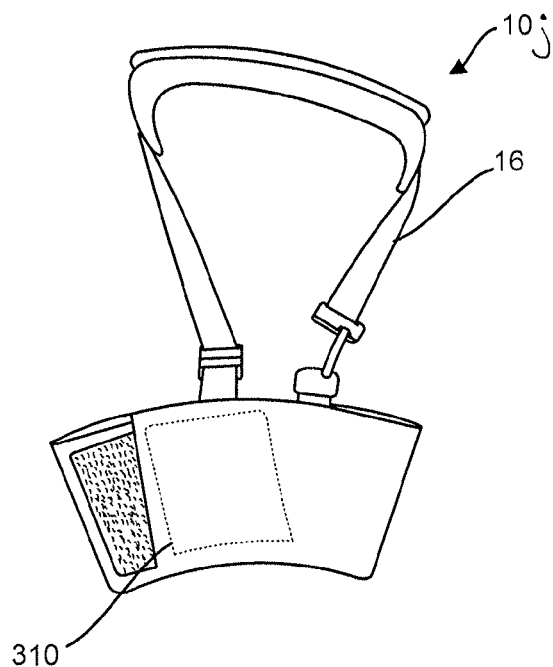
FIG. 16B illustrates a top view of the hand elevation device of FIG. 16A not being worn by a user.

FIGS. 16A and 16B illustrate another implementation of the hand elevation device 10j, which includes a neck strap 16 extending from an arm sleeve 310. The arm sleeve 310 can be configured to have an open-ended cone shape when assembled for use (as shown in FIGS. 16A and 16B). The open-ended cone shape can allow the user's bent elbow to extend through the open end, which can allow the user's forearm and upper arm to be supported in a bent configuration with the user's hand positioned above the elevation line 17. The arm sleeve 310 can include an attachment feature (e.g., Velcro, snaps, etc.) that allows the arm sleeve 310 to be adjusted for customized fitting for a user. The arm sleeve 310 can also include an attachment feature (e.g., Velcro, buckles, snaps, etc.) at one end of the neck strap 16 that allows the user to connect and disconnect the neck strap 16 to the arm sleeve 310.

FIGS. 17A-17B illustrate both sides of an embodiment of the hand elevation device 10w including features that allow the device to be used on either the left or right arm. For example, FIG. 17A shows a first side of the hand elevation device having a forearm support 20w with a first end including the elbow strap 110 and a strap connector 111. A second end of the forearm support 20w includes a part of the neck strap 16 extending therefrom. The forearm support 20w can be at least partially tubular or U-shaped with both ends or sides of the forearm support 20w including a strap connector, as shown in FIG. 17B. As such, a detachable part of the neck strap 16a can be coupled at one end to the neck strap extending from the second end of the forearm support 20w and releasably connected at the opposing end to the first end of the forearm support 20w at either of the strap connectors 111. Such coupling to either strap connector 111 depends on which hand the device 10n will support in the therapeutic position when in use.

For example, FIG. 17C illustrates the hand elevation device of FIGS. 17A-17B shown configured to be used on a right arm for supporting the user's right hand in the therapeutic position. In this configuration, the user can insert his head through the opening formed between the neck strap 16 and the forearm support 20w and slide the elbow adjacent the hand to be supported into the opening formed between the elbow strap 110 and the forearm support 20w. The strap connector 111 that is connected to the neck strap 16 will face the user's back such that strap connector 111 not connected to the neck strap 16 can be seen in a front view of the user wearing the device, as shown in FIG. 17D.

The neck strap 16 can include one or more indicators or markers 117 along a length of the neck strap 16. Such indicators 117 can allow a medical professional to modify the neck strap such that the device 10w is limited in use such that it can only be worn where the hand is secured in the therapeutic position. In some implementations, the neck strap can be long enough such that various other positions of the hand and/or wrist can be maintained. Various other features can be included in the device 10w, such as one or more pockets 119 along the forearm support 20w that can be used to insert therapeutic devices, such as heating or cooling packs for further assisting with treating the hand, wrist, and/or forearm.

Any of the implementations of the hand elevation device discussed or contemplated herein can be configured to position and maintain the position of the user's recovering arm in the therapeutic position, as described above. In addition, any of the implementations of the hand elevation device discussed or contemplated herein can be ambidextrous such that they can support either the left or right arm. For example, any of the implementations of the hand elevation device discussed or contemplated herein can be turned inside-out or reassembled for wearing on an opposite arm.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the claim(s) may include other implementations or embodiments.

What is claimed is:

1. A device for elevating a hand or wrist of a user comprising: a forearm support including an elongated body having a first part configured to support a forearm of the user and a second part configured to support the hand of the user, the forearm support configured to support the forearm and the hand in a first position, the first position including at least a part of the hand positioned above an elevation line, the elevation line including a horizontal line that intersects a part of the heart of the user, the forearm support including at least one first extension extending from the first part of the elongated body at a fixed first angle relative to a longitudinal axis of the forearm support, the forearm support including a pair of second extensions that each extend from the second part of the elongated body at a fixed second angle relative to a longitudinal axis of the forearm support; a neck strap including a first end and a second end, the first end of the neck strap extending directly and releasably from the at least one first extension of the forearm support, the first end of the neck strap extending from the at least one first extension at the fixed first angle, the neck strap being configured to extend around a part of a neck of the user and support the forearm support to allow the forearm support to support the forearm and the hand in the first position; and an elbow strap including a first coupling end and a second coupling end, the elbow strap extending between the pair of second extensions such that the first coupling end of the elbow strap is coupled to a first extension of the pair of second extensions and the second coupling end of the elbow strap is coupled to a second extension of the pair of second extensions, the elbow strap being adjustable in length between the pair of second extensions, the elbow strap configured to extend around a part of and support an upper arm of the user and allow an elbow of the user to be exposed and prevented from contact by the elbow strap and forearm support thereby preventing pressure applied to the elbow by the forearm support and/or elbow strap at least when the forearm support is supporting the forearm and the hand of the user in the first position, the elbow strap positioned parallel to the elevation line and being coupled to the second end of the neck strap to support the upper arm alongside a torso of the user.

2. The device of claim 1, wherein the elongated body includes opposing parallel sides.

3. The device of claim 1, wherein the elongated body includes opposing sides that are angled relative to each other.

4. The device of claim 1, wherein the fixed first angle is within 30 degrees to 60 degrees.

5. The device of claim 4, wherein the fixed second angle is within 110 degrees to 60 degrees.

6. The device of claim 1, wherein the first position includes a bend angle formed between a forearm longitudinal axis and an upper arm longitudinal axis, and wherein the bend angle is within a range of 45 degrees to 80 degrees.

7. The device of claim 1, wherein the first position includes a position angle formed between a forearm longitudinal axis and the horizontal line, and wherein the position angle is within a range of 20 degrees to 60 degrees.

8. The device of claim 1, wherein the first position includes an upper arm angle formed between an upper arm longitudinal axis and the horizontal line, and wherein the upper arm angle is within a range of 80 degrees to 100 degrees.

9. The device of claim 1, wherein the neck strap includes a length adjustment feature that allows the length of the neck strap to be adjusted.

10. The device of claim 9, wherein the length adjustment feature includes one or more of a lanyard, a clip, a hook and loop fastening system, and a pulley.

11. The device of claim 1, wherein the neck strap includes one or more indicators along a length of the neck strap.

12. The device of claim 1, wherein the device further includes at least one compartment for releasably coupling a thermal device to the forearm support.

13. The device of claim 1, wherein the device further includes a releasable connector that releasably connects the forearm support to the neck strap.

14. The device of claim 1, wherein the device is configured for use with either the left arm or the right arm.

15. The device of claim 1, wherein the device includes a cushion feature that is slidably coupled to the neck strap for positioning between the neck of the user and the neck strap.

16. A method comprising:

releasably coupling a positioning device to a user for elevating a hand or wrist of the user, the positioning device including:

a forearm support including an elongated body having a first part configured to support a forearm of the user and a second part configured to support the hand of the user, the forearm support configured to support the forearm and the hand in a first position, the first position including at least a part of the hand positioned above an elevation line, the elevation line including a horizontal line that intersects a part of the heart of the user, the forearm support including at least one first extension extending from the first part of the elongated body at a fixed first angle relative to a longitudinal axis of the forearm support, the forearm support including a pair of second extensions that each extend from the second part of the elongated body at a fixed second angle relative to a longitudinal axis of the forearm support;

a neck strap including a first end and a second end, the first end of the neck strap extending directly and releasably from the at least one first extension of the forearm support, the first end of the neck strap extending from the at least one first extension at the fixed first angle, the neck strap being configured to extend around a part of a neck of the user and support the forearm support to allow the forearm support to support the forearm and the hand in the first position; and an elbow strap including a first coupling end and a second coupling end, the elbow strap extending between the pair of second extensions such that the first coupling end of the elbow strap is coupled to a first extension of the pair of second extensions and the second coupling end of the elbow strap is coupled to a second extension of the pair of second extensions, the elbow strap being adjustable in length between the pair of second extensions, the elbow strap configured to extend around a part of and support an upper arm of the user and allow an elbow of the user to be exposed and prevented from contact by the elbow strap and forearm support thereby preventing pressure applied to the elbow by the forearm support and/or elbow strap at least when the forearm support is supporting the forearm and the hand of the user in the first position, the elbow strap positioned parallel to the elevation line and being coupled to the second end of the neck strap to support the upper arm alongside a torso of the user.

* * * * *